US011752271B2

(12) United States Patent
Boisdon et al.

(10) Patent No.: US 11,752,271 B2
(45) Date of Patent: Sep. 12, 2023

(54) DRUG DELIVERY APPARATUS

(71) Applicant: DESVAC, Saint-Barthelemy-d'Anjou (FR)

(72) Inventors: Olivier Boisdon, Saint-Barthelemy-d'Anjou (FR); Christophe Thomas-Javid, Beaucouze (FR); Stephane Veyrent, Saint-Barthelemy-d'Anjou (FR)

(73) Assignee: DESVAC, Saint-Barthelemy-d'Anjou (FR)

( * ) Notice: Subject to any disclaimer, the term of this patent is extended or adjusted under 35 U.S.C. 154(b) by 419 days.

(21) Appl. No.: 16/763,757

(22) PCT Filed: Nov. 15, 2018

(86) PCT No.: PCT/IB2018/001449
§ 371 (c)(1),
(2) Date: May 13, 2020

(87) PCT Pub. No.: WO2019/097298
PCT Pub. Date: May 23, 2019

(65) Prior Publication Data
US 2020/0384204 A1    Dec. 10, 2020

Related U.S. Application Data

(60) Provisional application No. 62/586,478, filed on Nov. 15, 2017.

(51) Int. Cl.
*A61M 5/315*    (2006.01)
*A61M 5/31*    (2006.01)

(52) U.S. Cl.
CPC .... *A61M 5/31546* (2013.01); *A61M 5/31568* (2013.01); *A61M 5/31573* (2013.01);
(Continued)

(58) Field of Classification Search
CPC .. A61M 2205/3317; A61M 2205/3375; A61M 5/31568; A61M 5/31573;
(Continued)

(56) References Cited

U.S. PATENT DOCUMENTS 5,307,263 A    4/1994    Brown
5,569,212 A *  10/1996   Brown .............. A61M 5/31525
                                                    604/207
(Continued)

FOREIGN PATENT DOCUMENTS

CN    101268336 A    9/2008
CN    101484953 A    7/2009
(Continued)

OTHER PUBLICATIONS

International Search Report dated Apr. 9, 2019 in PCT/IB2018/001449 filed on Nov. 15, 2018.
(Continued)

*Primary Examiner* — Nilay J Shah
(74) *Attorney, Agent, or Firm* — Oblon, McClelland, Maier & Neustadt, L.L.P.

(57) ABSTRACT

A drug delivery apparatus including a barrel to contain a substance, a piston slidable in the barrel, a supply circuit to provide input currents, an antenna affixed along the barrel to receive the input current, generate inductance with the piston, and provide output currents commensurate with a position of the piston along the piston course, and processing circuitry configured to receive the output currents, and determine a quantity of the substance inside the barrel based on the output currents.

20 Claims, 15 Drawing Sheets

(52) U.S. Cl.
CPC ............... *A61M 2005/3125* (2013.01); *A61M 2005/31588* (2013.01); *A61M 2205/3317* (2013.01); *A61M 2205/3375* (2013.01); *A61M 2205/3561* (2013.01); *A61M 2205/6054* (2013.01); *A61M 2250/00* (2013.01)

(58) Field of Classification Search
CPC .... A61M 5/31546; A61M 2005/31588; A61M 2205/3561; A61M 2205/6054; A61M 2250/00; A61M 2205/50; G16H 10/65; G16H 2250/00; G16H 2205/50
See application file for complete search history.

(56) References Cited

U.S. PATENT DOCUMENTS

| | | | | |
|---|---|---|---|---|
| 5,628,309 | A * | 5/1997 | Brown | A61M 5/31525 600/310 |
| 5,651,775 | A * | 7/1997 | Walker | A61M 5/31533 604/207 |
| 5,704,922 | A * | 1/1998 | Brown | A61M 5/31525 604/207 |
| 5,720,733 | A * | 2/1998 | Brown | A61M 5/1782 222/23 |
| 5,782,814 | A * | 7/1998 | Brown | A61M 5/00 604/207 |
| 5,792,117 | A * | 8/1998 | Brown | A61M 5/31546 604/207 |
| 6,068,615 | A * | 5/2000 | Brown | A61M 5/1782 604/207 |
| 6,110,148 | A * | 8/2000 | Brown | A61M 5/1782 222/23 |
| 2004/0015123 | A1 * | 1/2004 | Smith | A61M 5/204 604/65 |
| 2005/0007296 | A1 | 1/2005 | Endo et al. | |
| 2006/0065713 | A1 * | 3/2006 | Kingery | A61M 5/1415 235/380 |
| 2006/0229551 | A1 * | 10/2006 | Martinez | G16H 20/17 604/67 |
| 2007/0066940 | A1 * | 3/2007 | Karunaratne | A61M 5/172 604/152 |
| 2007/0093752 | A1 * | 4/2007 | Zhao | A61M 5/172 604/131 |
| 2009/0112160 | A1 * | 4/2009 | Yang | A61J 15/0076 604/113 |
| 2009/0318876 | A1 * | 12/2009 | Hansen | A61M 5/24 604/187 |
| 2011/0270188 | A1 | 11/2011 | Caffey et al. | |
| 2011/0275410 | A1 | 11/2011 | Caffey et al. | |
| 2011/0275987 | A1 | 11/2011 | Caffey et al. | |
| 2012/0041427 | A1 | 2/2012 | Caffey et al. | |
| 2013/0281965 | A1 | 10/2013 | Kamen et al. | |
| 2015/0174330 | A1 | 6/2015 | Nagel et al. | |
| 2016/0038266 | A1 | 2/2016 | Edwards | |
| 2017/0182251 | A1 | 6/2017 | Nagel et al. | |
| 2017/0197037 | A1 | 7/2017 | Edwards | |

FOREIGN PATENT DOCUMENTS

| | | | | |
|---|---|---|---|---|
| CN | 101951975 | A | 1/2011 | |
| CN | 105007961 | A | 10/2015 | |
| CN | 205593543 | U | 9/2016 | |
| CN | 106470717 | A | 3/2017 | |
| CN | 107257696 | A | 10/2017 | |
| CN | 101132821 | A | 2/2021 | |
| DE | 10 2015 220 905 | A1 | 4/2017 | |
| JP | 2015-518747 | A | 7/2015 | |
| WO | WO-9803215 | A1 * | 1/1998 | ............ G01F 11/027 |
| WO | WO-2008003625 | A1 * | 1/2008 | .............. A61M 5/24 |
| WO | WO 2011/133724 | A2 | 10/2011 | |
| WO | WO 2014/107766 | A1 | 7/2014 | |
| WO | WO 2016/202339 | A1 | 12/2016 | |

OTHER PUBLICATIONS

Combined Russian Office Action and Search Report dated Dec. 17, 2021 in Russian Patent Application No. 2020119412 (with English translation), 19 pages.

Chinese Office Action dated Jun. 6, 2022 in Chinese Patent Application No. 201880074103.9 (with English language translation), 8 pages.

Colombian Office Action and Search Report dated Jun. 14, 2022 in Colombian Patent Application No. NC2020/0005955 (with English language translation), citing documents 1-2 therein, 25 pages.

Chilean Office Action dated Mar. 14, 2022 in Chilean Patent Application No. 1280-2020, 14 pages.

Combined Chinese Office Action and Search Report dated Oct. 26, 2021 in Chinese Patent Application No. 201880074103.9 (with English translation), citing documents AA and AO-AU therein, 21 pages.

Combined Chilean Office Action and Search Report dated Nov. 15, 2021 in Chilean Patent Application No. 202001280, 14 pages.

Office Action dated Sep. 20, 2022, in corresponding Brazilian Patent Application No. 11 2020 009635 0 (with Partial English Translation), 6 pages.

Combined Chinese Office Action and Search Report dated Oct. 21, 2022 in Chinese Patent Application No. 201880074103.9 (with unedited computer generated English Translation), citing references 15-17 therein, 20 pages.

Office Action dated Mar. 6, 2023, in corresponding Vietnamese Patent Application No. 1-2020-03243 (with English Translation), 3 pages.

International Preliminary Report on Patentability and Written Opinion dated May 19, 2020, in PCT/IB2018/001449, 9 pages.

Notice of Reasons for Rejection dated Oct. 25, 2022 in Japanese Patent Application No. 2020-544997 (with English language translation), citing document 15 therein, 11 pages.

Office Action dated Mar. 14, 2023 in Chinese Patent Application No. 201880074103.9 with concise English translation.

Office Action dated May 16, 2023 in Japanese Patent Application No. 2020-544997 with concise English translation.

* cited by examiner

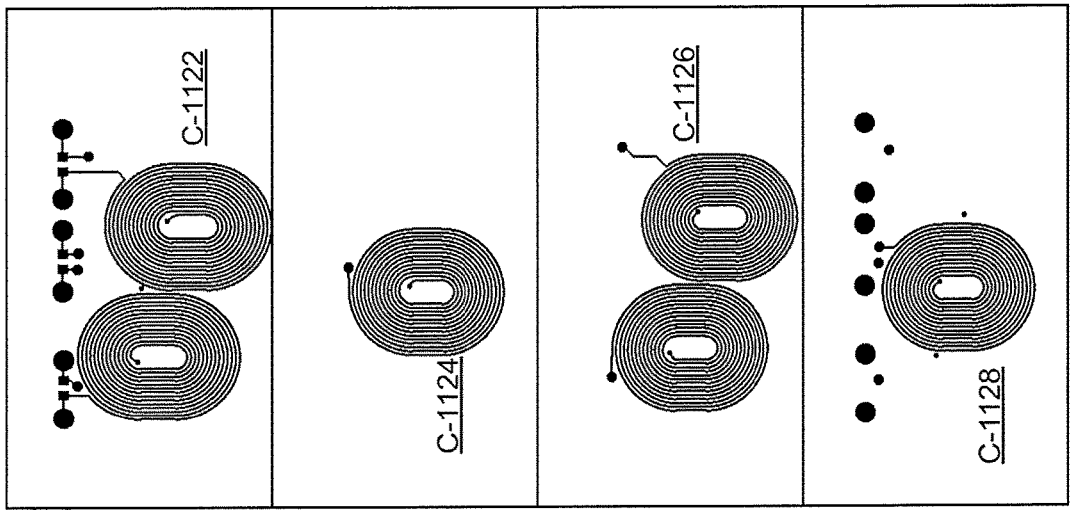
Fig. 4D — 4th Configuration
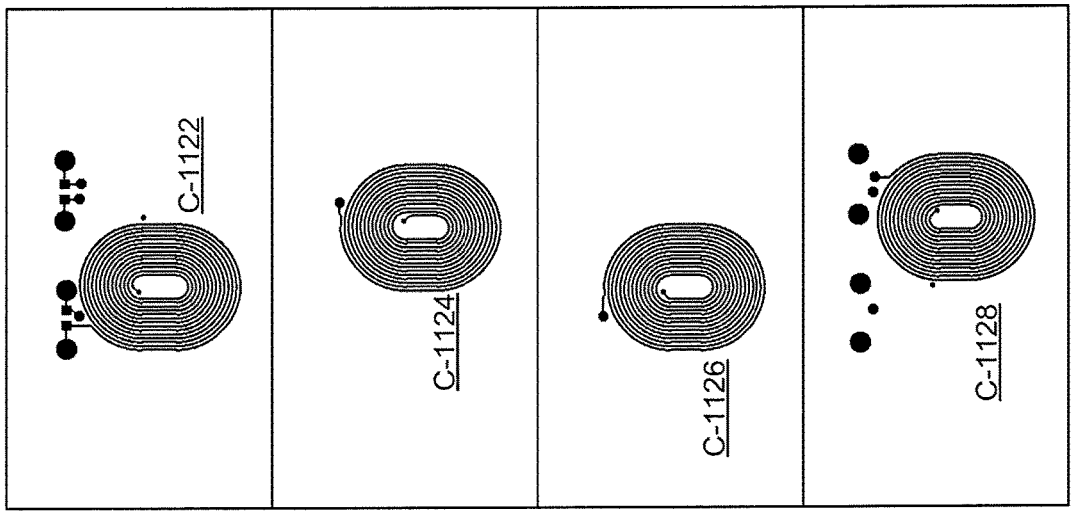
Fig. 4E — 5th Configuration
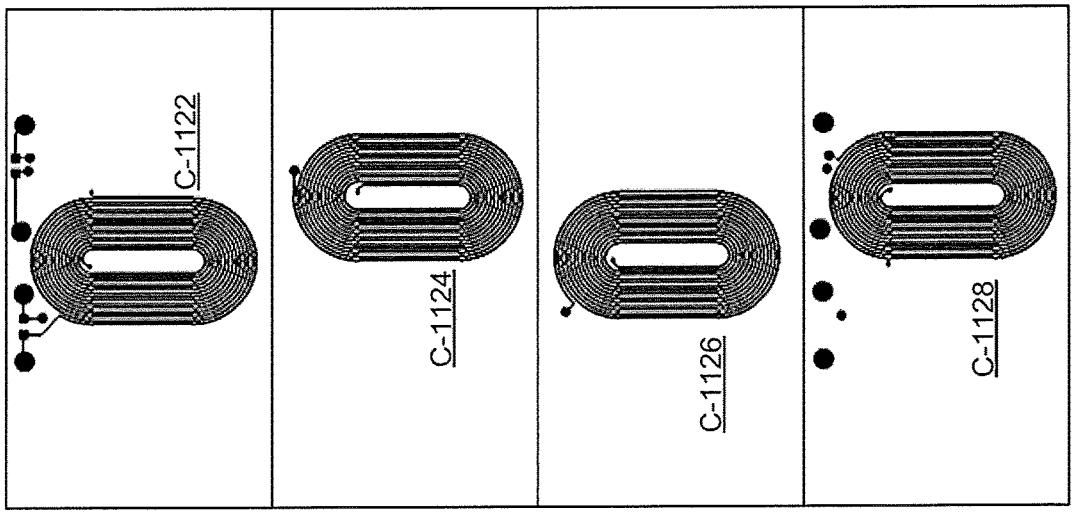
Fig. 4F — 6th Configuration

DRUG DELIVERY APPARATUS

CROSS-REFERENCE TO RELATED APPLICATIONS

The present application claims priority to U.S. Provisional Application No. 62/586,478, filed Nov. 15, 2017, the entire contents of which are hereby incorporated by reference.

BACKGROUND

Field of the Disclosure

The present disclosure relates to drug delivery apparatus and notably to parenteral drug administration systems.

Description of the Related Art

Delivering administrating substances, e.g. powerful drugs, to a target, e.g. an animal or a patient, often requires to precisely know the quantity that is delivered and/or administered to prevent overdosages or underdosages from occurring.

To this end, syringes with graduated marks on a transparent barrel are often employed to measure an amount of substance to be delivered and/or delivered.

However, quantifying the volume of the substance delivered by visually inspecting the graduated marks may lack precision and depending on the situation, e.g. clear and/or transparent substance and/or an environment lacking luminosity, and/or substance leaving traces that make visual perception of the graduated marks difficult, may be not even be possible.

Thus, a drug delivery apparatus that can precisely quantify the amount of drug administered and overcome the above-mentioned limitations is desired.

SUMMARY

Accordingly, an object of the present disclosure is to provide a drug delivery apparatus which overcomes the above-mentioned limitations.

In one non-limiting illustrative example, a drug delivery apparatus is presented. The drug delivery apparatus includes a barrel to contain a substance, a piston slidable in the barrel along a piston course, a supply circuit to provide input currents, an antenna affixed along the barrel including a printed circuit board with a plurality layers stacked on top of each other and connected to the supply circuit, and a plurality of coils printed on the plurality of layers to receive the input currents, generate an inductance with the piston, and provide output currents commensurate with the inductance, a target identifier to detect a target marker and provide target reading signals commensurate with target information, a substance identifier to read a substance marker and provide substance reading signals commensurate with substance information, and processing circuitry configured to receive the output currents, the target reading signals, and the substance reading signals, determine a quantity of the substance inside the barrel based on the output currents, extract the target information based on the target reading signals, and extract the substance information based on the substance reading signals.

In one non-limiting illustrative example, a drug delivery apparatus is presented. The drug delivery apparatus includes a barrel to contain a substance, a piston slidable in the barrel along a piston course, a supply circuit to provide input currents, an antenna affixed along the barrel including a printed circuit board with a plurality of layers stacked on top of each other and connected to the supply circuit, and a plurality of coils printed on the plurality of layers to receive the input currents, generate an inductance with the piston, and provide output currents commensurate with the inductance, and processing circuitry connected to the plurality of coils and configured to receive the output currents, and determine a quantity of the substance inside the barrel based on the output currents.

In one non-limiting illustrative example, a drug delivery apparatus is presented. The drug delivery apparatus includes a barrel to contain a substance, a piston slidable in the barrel along a piston course, a supply circuit to provide input currents, an antenna affixed along the barrel to receive the input currents, generate an inductance with the piston, and provide output currents commensurate with the inductance; and processing circuitry configured to receive the output currents, and determine a quantity of the substance inside the barrel based on the output currents.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

FIG. 4D is a schematic view of a fourth exemplary coil configuration of the antenna, according to certain aspects of the disclosure;

FIG. 4E is a schematic view of a fifth exemplary coil configuration of the antenna, according to certain aspects of the disclosure;

FIG. 4F is a schematic view of a sixth exemplary coil configuration of the antenna, according to certain aspects of the disclosure;

DETAILED DESCRIPTION

Figure 1A:
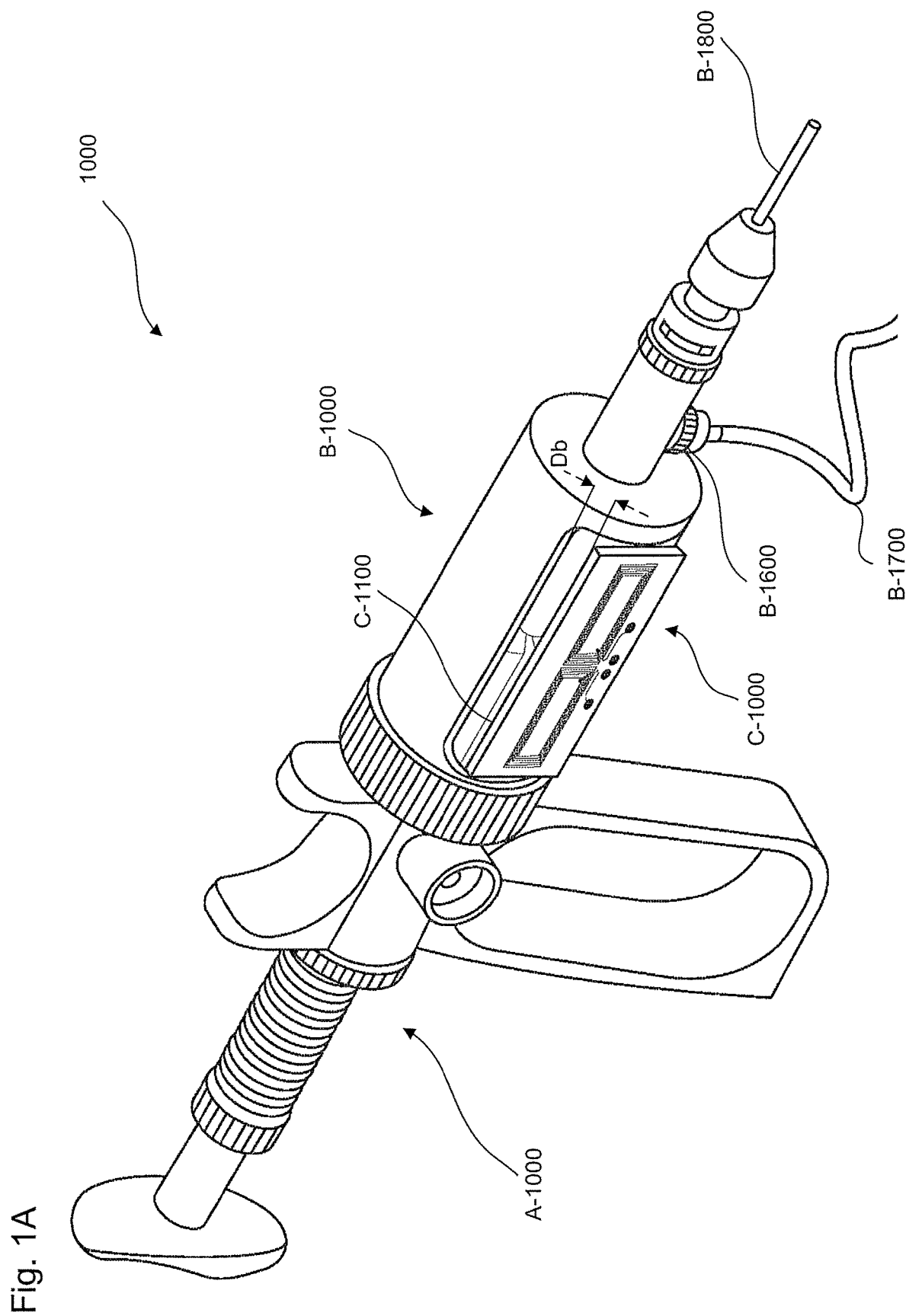
FIG. 1A is a perspective view of the drug delivery apparatus, according to certain aspects of the disclosure.

All publications, patent applications, patents, and other references mentioned herein are incorporated by reference in their entirety. Further, the materials, methods, and examples discussed herein are illustrative only and are not intended to be limiting.

In the drawings, like reference numerals designate identical or corresponding parts throughout the several views. Further, as used herein, the words "a", "an", and the like include a meaning of "one or more", unless stated otherwise. The drawings are generally drawn not to scale unless specified otherwise or illustrating schematic structures or flowcharts.

To increase measurement precision of the substance administered, drug delivery apparatuses relying on mechanical and/or electromechanical systems, such as syringe pumps, have been used. Although these drug delivery apparatuses may be used, they present numerous drawbacks. Notably, for such drug delivery apparatuses, quantification is performed through electromechanical measurement systems, e.g. electric step motors, tachometers, speed sensors, or the like, that actuate the syringes by small and known increments which may result in a measurement of the amount of substance delivered. However, these systems can be cumbersome, heavy, and require connection to a power grid which renders them impractical for field use such as livestock vaccination or other medicinal treatment. In addition, these systems can be cost prohibitive as the electromechanical measurement systems on which they relied can be expensive to manufacture. Furthermore, these systems may require specific syringes and/or modification of already available syringes.

The drug delivery apparatus of the present disclosure provides quantification of the substance delivered by relying on inductance interactions to localize a piston that pushes the substance.

The drug delivery apparatus of the present disclosure provides numerous advantages over other systems. For example, the drug delivery apparatus provides a quantification of the substance delivered that is external, noninvasive, and without contact with the substance to deliver and consequently does not affect the substance, e.g. the apparatus does not heat, discolor, and/or contaminate the substance to deliver. In another example, the disclosed drug delivery apparatus provides a quantification of the substance delivered that is independent of the substance's physical characteristics, e.g. color, adherence to surface and soiling, and that can be integrated with conventional dispensing mechanisms, e.g. syringes, without modification or limited modifications.

Figure 1B:
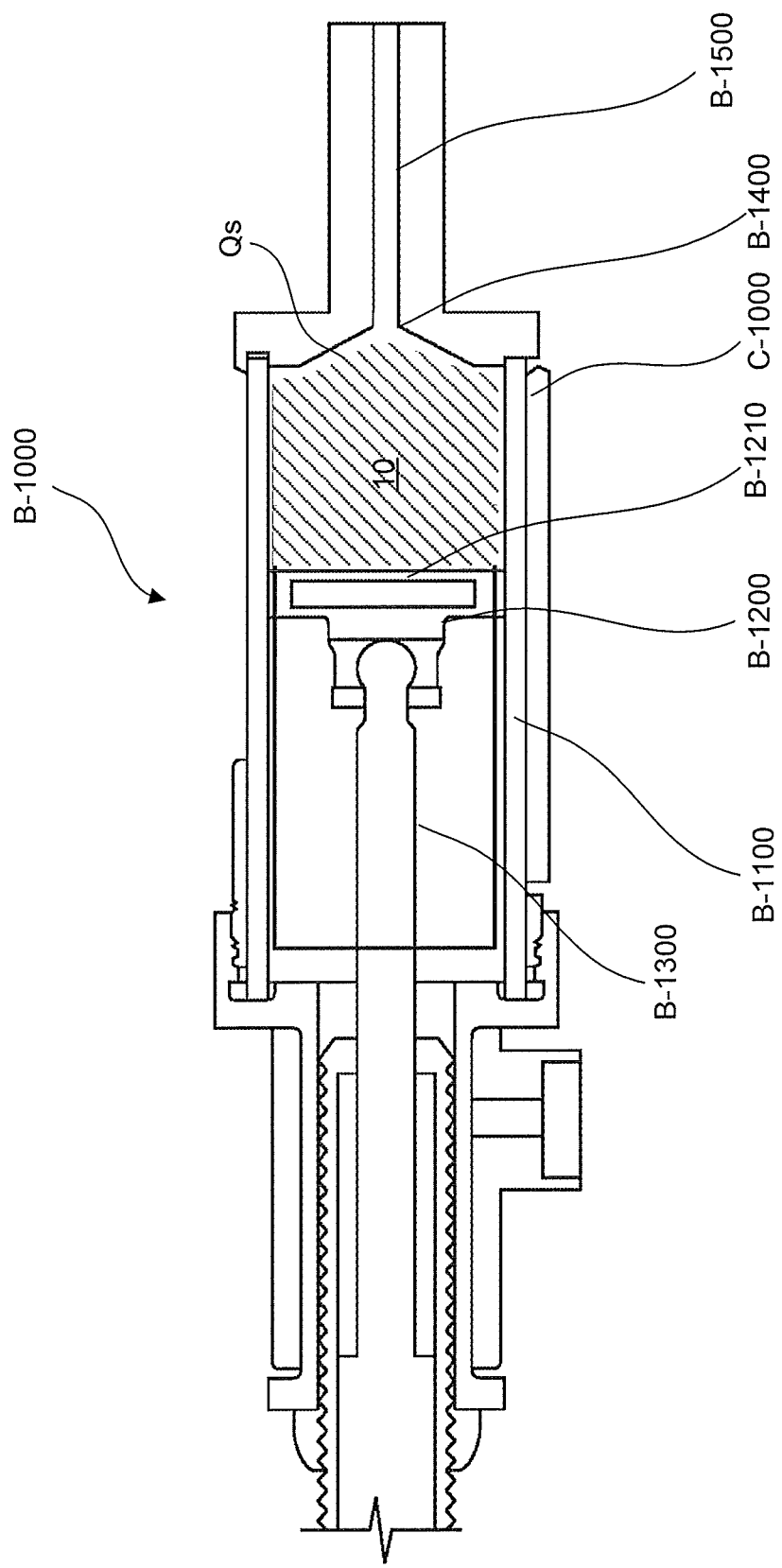
FIG. 1B is a cross sectional view of the drug delivery apparatus, according to certain aspects of the disclosure.

FIGS. 1A-1B are a perspective view and a cross sectional view of a drug delivery apparatus 1000, according to certain aspects of the disclosure.

The drug delivery apparatus 1000 can include a stock A-1000, a dispensing mechanism B-1000 mounted on the stock A-1000, and a measuring system C-1000 affixed along the dispensing mechanism B-1000.

Figure 5:
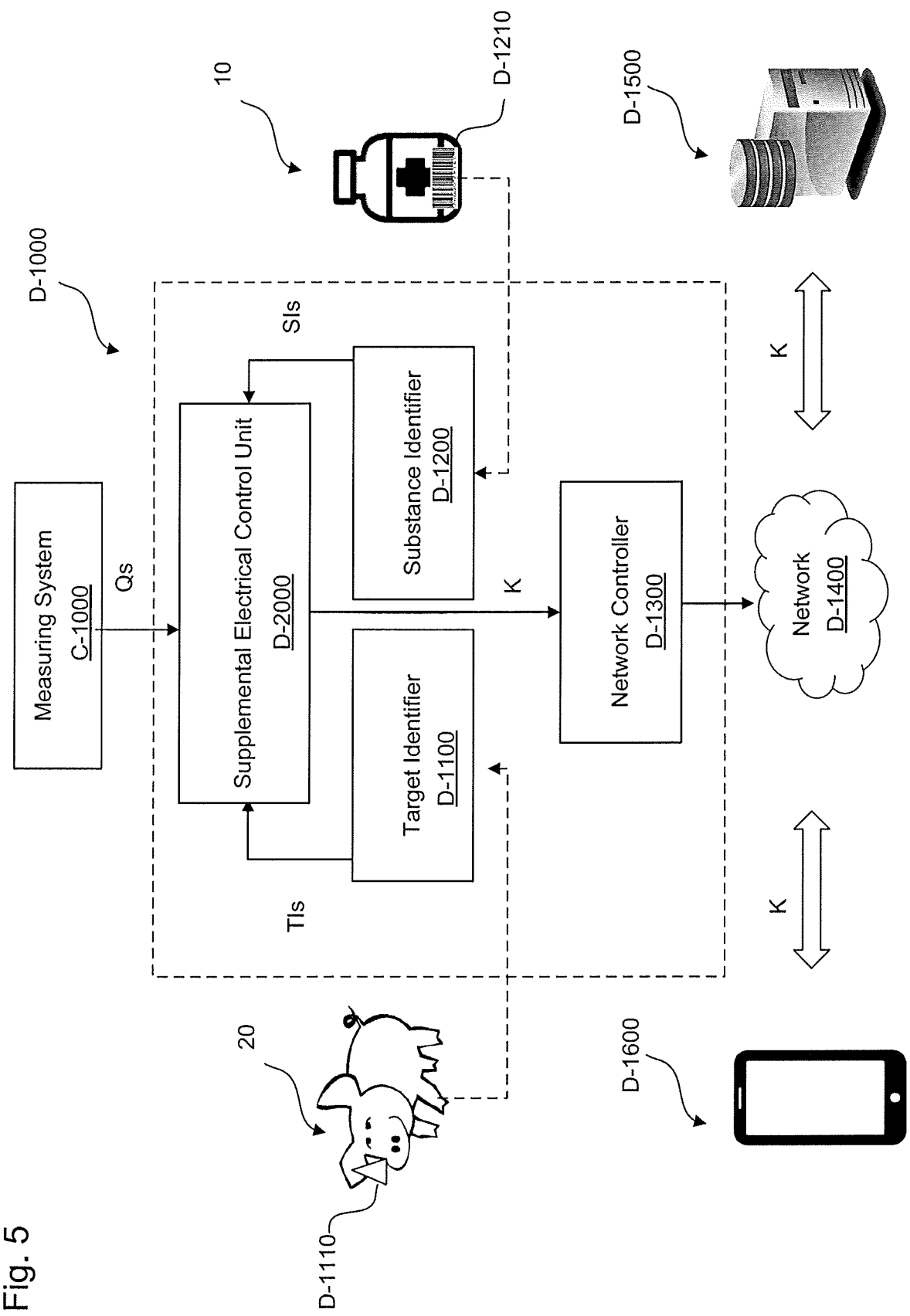
FIG. 5 is a schematic view of a tracking system of the drug delivery apparatus, according to certain aspects of the disclosure.

The dispensing mechanism B-1000 can extract, withhold, and/or discharge a substance 10 to be administered to a target 20, see FIG. 5, such as a livestock animal including a pig, among others. The substance 10 can be administered to the target 20 to feed, treat, cure, prevent, diagnose a disease, perform tests and/or euthanize, or in general to affect the well-being of the target 20 and be a medicine, an antibiotic, a vaccine, a mixture of nutrients, or any pharmaceutical products. The substance 10 can be in the form of a liquid, a gas, and/or solid particles suspended in a liquid.

The measuring system C-1000 can quantify a substance quantity Qs being extracted and/or discharged by the drug delivery apparatus 1000.

The stock A-1000 can provide support for the dispensing mechanism B-1000 and/or the measuring system C-1000 as well as ergonomic features, e.g. a handle, a trigger, a pullback lever, or the like, for manipulating, transporting, and/or operating the drug delivery apparatus 1000 by a user.

The drug delivery apparatus 1000 can provide quantification of the substance 10 extracted and discharged by the dispensing mechanism B-1000 while minimizing resources, e.g. space, energy consumption, and/or weight, allocated to quantify the substance 10 extracted and discharged by the dispensing mechanism B-1000.

Such a quantification of the substance 10 extracted and discharged by the dispensing mechanism B-1000 is performed by relying on quantifications and/or detections of contactless interactions between the dispensing mechanism B-1000 and the measuring system C-1000.

The contactless interactions can correspond to any interactions that do not require physical contact between the dispensing mechanism B-1000 and the measuring system C-1000 to generate quantifiable values that depend on the quantify of the substance 10 discharged by the dispensing mechanism B-1000 and notably based on displacement of a piston B-1200 of the dispensing mechanism B-1000.

In one example, the contactless interactions can correspond to inductance variations generated by movable parts of the dispensing mechanism B-1000 onto coils of the measuring system C-1000 and/or onto inductive sensors, e.g. inductive linear variable differential transformer sensors from Micro-Epsilon, of the measuring system C-1000.

In another example, the contactless interactions can correspond to magnetic field variations generated by a magnet affixed to movable parts and/or by the movable parts itself of the dispensing mechanism B-1000 onto magnetic sensors, e.g. Hall effect sensors, and/or eddy sensors from Micro-Epsilon, of the measuring system C-1000.

In another example, the contactless interactions can correspond to magneto-inductive interactions generated by a magnet affixed to movable parts of the dispensing mechanism B-1000 onto magneto-inductive sensors, e.g. Magneto-inductive displacement sensors from Micro-Epsilon, of the measuring system C-1000.

In another example, the contactless interactions can correspond to sonic interactions generated by microwave radiations emitted from the measuring system C-1000 and movable parts of the dispensing mechanism B-1000 that reflect the microwave radiations back to the measuring system C-1000 with phase shifts depending on positions of the moveable parts.

In another example, the contactless interactions can correspond to optical interactions between lights emitted from the measuring system C-1000 and optical markers, e.g. light reflectors, positioned on movable parts of the dispensing mechanism B-1000 that reflect lights back to the measuring systems C-1000 with reflective angles depending on positions of the moveable parts.

In another example, the contactless interactions can correspond to optical interactions between lights emitted externally from the measuring system C-1000 and directed at a target. For instance, the light emitted from the measuring system C-1000 can be emitted with known properties, including, among others, an emission angle, toward the target. Said emission angle can be evaluated in context of a reception angle determined when said emitted light is reflected back to and received at the measuring system C-1000. In an example, the emitted light is infrared light and the reflected light is reflected by a target or, for instance, an animal. By determining the change in an angle of emission from an angle of reception, the angle at which a needle B-1800, and the dispensing mechanism B-1000, writ large, contact the target can be calculated. By comparing said calculated contact angle with a known level of tolerance understood, for example, at the level of a server, to provide quality injections, an alert can be provided to the user of the dispensing mechanism B-1000 that the approach may lead to an inappropriate contact angle and ineffective administration of the substance. In another example, the dispensing mechanism B-1000 can be deactivated in response to a determination that the contact angle is not appropriate. In this case, the actuating component of the dispensing mechanism B-1000 can be controlled such that it only expels a substance when the contact angle is within an acceptable range. The above described determinations and calculations can be performed by hardware described in the context of the measuring system C-1000 of FIG. 2 or, generally, FIG. 5.

The dispensing mechanism B-1000 can include a barrel B-1100, a piston B-1200 slidably inserted inside the barrel B-1100, a plunger B-1300 connected to the piston B-1200 and protruding partially from the barrel B-1100, an opening B-1400 facing the piston B-1200, and a plain tip B-1500 protruding from the opening B-1400.

The plunger B-1300 can be actuated to slide the piston B-1200 inside the barrel B-1100 along a piston course L in a first direction, e.g. towards the opening B-1400, to push the substance 10 through the opening B-1400 and the opening B-1400 and discharge the substance 10 from the drug delivery apparatus 1000, or in a second direction, e.g. away from the opening B-1400, to pull the substance 10 through the opening B-1400 and extract the substance 10 from the external environment.

The actuation of the plunger B-1300 can be performed manually by the user or mechanically through an electrical actuator, e.g. an electrical motor rotating a lead screw that pushes and/or pulls the plunger B-1300, and/or a hydraulic and/or pneumatic actuator, e.g. compressed gas that pushes and/or pulls the plunger B-1300. According to an embodiment, the actuation of the electrical actuator can be controlled by processing circuitry local to the drug delivery apparatus 1000 and programmed to control the actuation of the electrical actuator in response to pre-determined conditions being satisfied. The specialized processing circuitry can be contained interchangeably within an electrical control unit or a supplemental electrical control unit. Further to the point, the specialized processing circuitry can be contained interchangeably within a remote server (for example, server (and database)), thereby providing remote control of the dispensing mechanism B-1000 of the drug delivery apparatus 1000 responsive to transmitted information.

The barrel B-1100 can be made of chemically resistant and electrically insulating materials, such as glass, ceramic, and/or plastic alloys, e.g. polyethylene alloys, to prevent inductance interactions between the barrel B-1100 and the measuring system C-1000 from happening.

The piston B-1200 can be made of chemically resistant and electrically conductive materials, such as stainless steel alloys, and/or other metallic alloys to provide inductance interactions between the piston B-1200 and the measuring system C-1000.

Alternatively, the piston B-1200 can be made of insulating materials, e.g. plastic alloys, but an inductance marker B-1210 made of electrically conductive materials can be affixed and/or enclosed in the piston B-1200 to provide inductance interactions between the inductance marker B-1210 and the measuring system C-1000.

The opening B-1400 can be configured to receive a needle B-1800 to facilitate the injection and/or extraction of the substance 10 in and/or from the target 20.

In addition, the opening B-1400 can include an inlet B-1600 connectable to a conduit B-1700 to combine a supplementary substance with the substance 10.

FIG. 2 is a schematic view of the measuring system C-1000 of the drug delivery apparatus 1000, according to certain aspects of the disclosure.

The measuring system C-1000 can include a supply circuit C-1300, an antenna C-1100 affixed along the barrel B-1100 and electrically connected to the supply circuit C-1300, a data acquisition circuitry C-1400 electrically connected to the antenna C-1100, and an electrical control unit C-1200 electrically connected to the data acquisition circuitry C-1400.

The supply circuit C-1300 can provide to the antenna C-1100 input signals Is, the antenna C-1100 can receive the input signals Is and generate an electromagnetic field M commensurate to the input signals Is, the electromagnetic field M can interact with the piston B-1200 of the dispensing mechanism B-1000 and can induce the antenna C-1100 to produce a one or more feedback signals Os commensurate with a piston position X and/or change of position along the piston course L, the data acquisition circuitry C-1400 can read the one or more feedback signals Os and provide physical values of the one or more feedback signals Os, and the electrical control unit C-1200 can receive the physical values and through software instructions provide values of the piston position X.

For example, the input signals Is can be oscillating currents produced by LC circuitry of the supply circuitry and the one or more feedback signals Os can be induced currents characterized by a resonant frequency Fr dependent on the piston position X along the piston course L.

Alternatively, the dispensing mechanism B-1000 including the piston B-1200 and/or the inductance marker B-1210 can have an electromagnetic permeability substantially lower than the electromagnetic permeability of the substance 10 to have the antenna C-1100 and/or the supply circuit C-1300 generating an amplitude of electromagnetic field M sufficiently large to interact mostly with the substance 10 as compared to the interaction with the piston B-1200 and/or the inductance marker B-1210.

According to an embodiment, the above-described approaches for determining the position of the piston B-1200, for instance, can be further exploited to quantify a substance 10 dispensed and, therefrom, provide an alert if the amount dispensed is equal to, less than, or greater than a prescribed dosage. For example, if the piston B-1200 position, as determined by the measuring system C-1000, is less than a prescribed piston position, therefore resulting in underdosage of the target, or animal, an alert can be provided such that additional substance 10 or, for instance, antibiotic, is provided. Additionally, in this case, a control signal (from local or remote processing circuitry) can be sent to the dispensing mechanism B-1000 to continue dispensing antibiotic until the quantity matches a prescribed dosage. In another example, if the piston B-1200 position is, as determined by the measuring system C-1000, equal to a position corresponding to a prescribed dosage of a substance 10, an alert can be provided to confirm that the proper substance 10 amount has been dispensed. Similarly to the above, in such a case that it is determined that a prescribed dosage is met before dispensing has completed, a control signal can be sent to the dispensing mechanism B-1000 to deactivate the electrical actuator. The prescribed dosage can be determined from target identification data and substance identification data. Such data will be described in detail with reference to FIG. 5.

The data acquisition circuitry C-1400 can be any type of circuitry configured to receive electrical signals and provide physical values characterizing the electrical signals such as intensity, voltage, and/or frequency. For example, the data acquisition circuitry C-1400 can be the board LDC1612EVM manufactured by Texas Instruments or similar circuitry.

In addition, the measuring system C-1000 can include a noise filter C-1500 to reduce extrinsic and/or intrinsic electrical perturbations, e.g. the electrical actuator of the plunger B-1300, and enhance the accuracy of the quantification of the substance 10. The noise filter C-1500 can be any type of active or passive noise filters. For example, the noise filter can be ferrite beads placed on electrical connections between the elements of the measuring system C-1000, e.g. the antenna C-1100, the supply circuit C-1300, the data acquisition circuitry C-1400, and/or the electrical control unit C-1200, and a ground connection between the data acquisition circuitry C-1400 and the dispensing mechanism B-1000.

Figure 2:
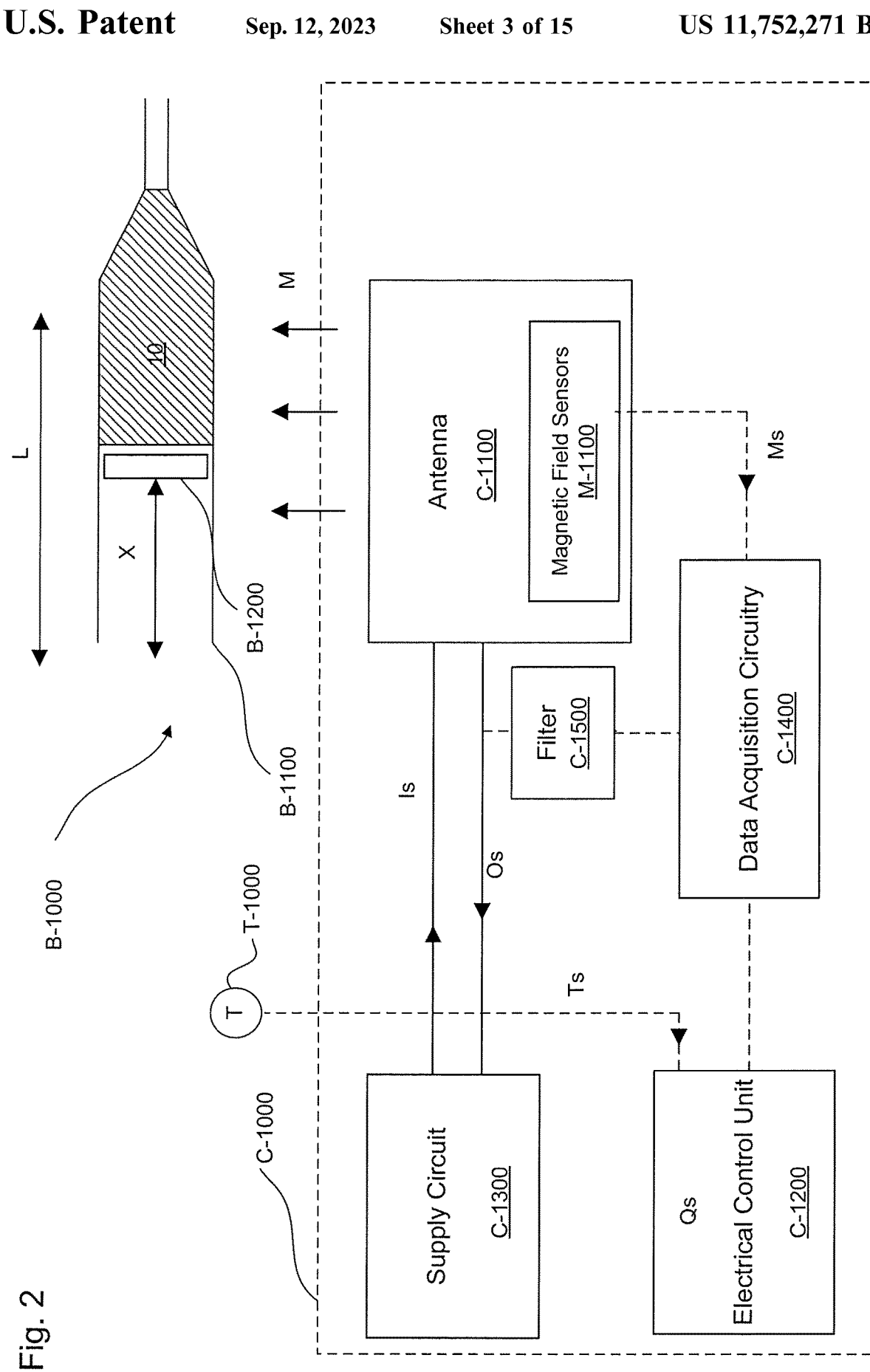
FIG. 2 is a schematic view of a measuring system of the drug delivery apparatus, according to certain aspects of the disclosure.

Furthermore, the measuring system C-1000 and/or other elements of the drug delivery apparatus 1000, e.g. the stock A-1000, and/or the dispensing mechanism B-1000, can include other features and/or structures to reduce and/or eliminate perturbations that can influence the quantification of the substance 10, e.g. room and/or environmental temperature variations, external fields generated by surrounding objects, animals, and/or body parts, and/or any other types of perturbations generated by mechanical and/or electrical interactions. For example, the measuring system C-1000 can include temperature sensors T-1000, e.g. thermistors, that provide temperature signals Ts commensurate with temperature of the environment, as illustrated in FIG. 2, and the electrical control unit C-1200 can be further configured to receive the temperature signals and the feedback signals Os and calculate the piston position X of the piston B-1200 based on the temperature signals and the feedback signals Os.

In another example, the temperature sensors T-1000 can be exploited to maximize the efficacy of a substance or, for instance, an antibiotic. For instance, the measuring system C-1000 can include temperature sensors T-1000 (e.g. thermistors) that provide temperature signals Ts commensurate with an environmental temperature or a temperature of the antibiotic within the dispensing mechanism B-1000. The electrical control unit C-1200 can be further configured to receive temperature signals and the feedback signals Os and determine, for instance, an efficacy of an antibiotic therefrom.

For example, there may be a case where it is known that an elevated external temperature exists within an animal facility and, as a result, animals, or targets, therein may have an elevated body temperature. An increase in body temperature of the animals may increase stress levels and negatively impact efficacy of the antibiotic. Accordingly, as this is determined, an alert can be provided to the user and the room temperature can be automatically modified. Further, the processing circuitry can be configured to send a control signal to the dispensing mechanism B-1000 to deactivate the electrical actuator and, effectively, lock out the drug delivery apparatus 1000 from administrating any substance, or, for instance, antibiotic.

In another example, the temperature sensors T-1000 can be used to determine the temperature of the substance, or, for instance, antibiotic, within the dispensing mechanism B-1000, the measuring system C-1000 thereby determining the temperature of the antibiotic within the context of antibiotic storage and transport specifications. For instance, if the temperature of the antibiotic within the dispensing mechanism B-1000 is elevated beyond an allowable temperature, correlating to a drop in efficacy of the antibiotic, an alert can be provided such that the antibiotic can be replaced. Further, the processing circuitry can be configured to send a control signal to the dispensing mechanism B-1000 to deactivate the electrical actuator.

In another example, the measuring system C-1000 can include a shield positioned on a back portion of the antenna C-1100 to shield the antenna C-1100 from external fields. In another example, the electrical control unit C-1200 can be further configured to perform calibration and/or take into account imprecisions linked to mechanical and/or electrical interactions e.g. play between the piston B-1200 and the barrel B-1100, imprecisions in inductance readings, or the like.

Figure 8:
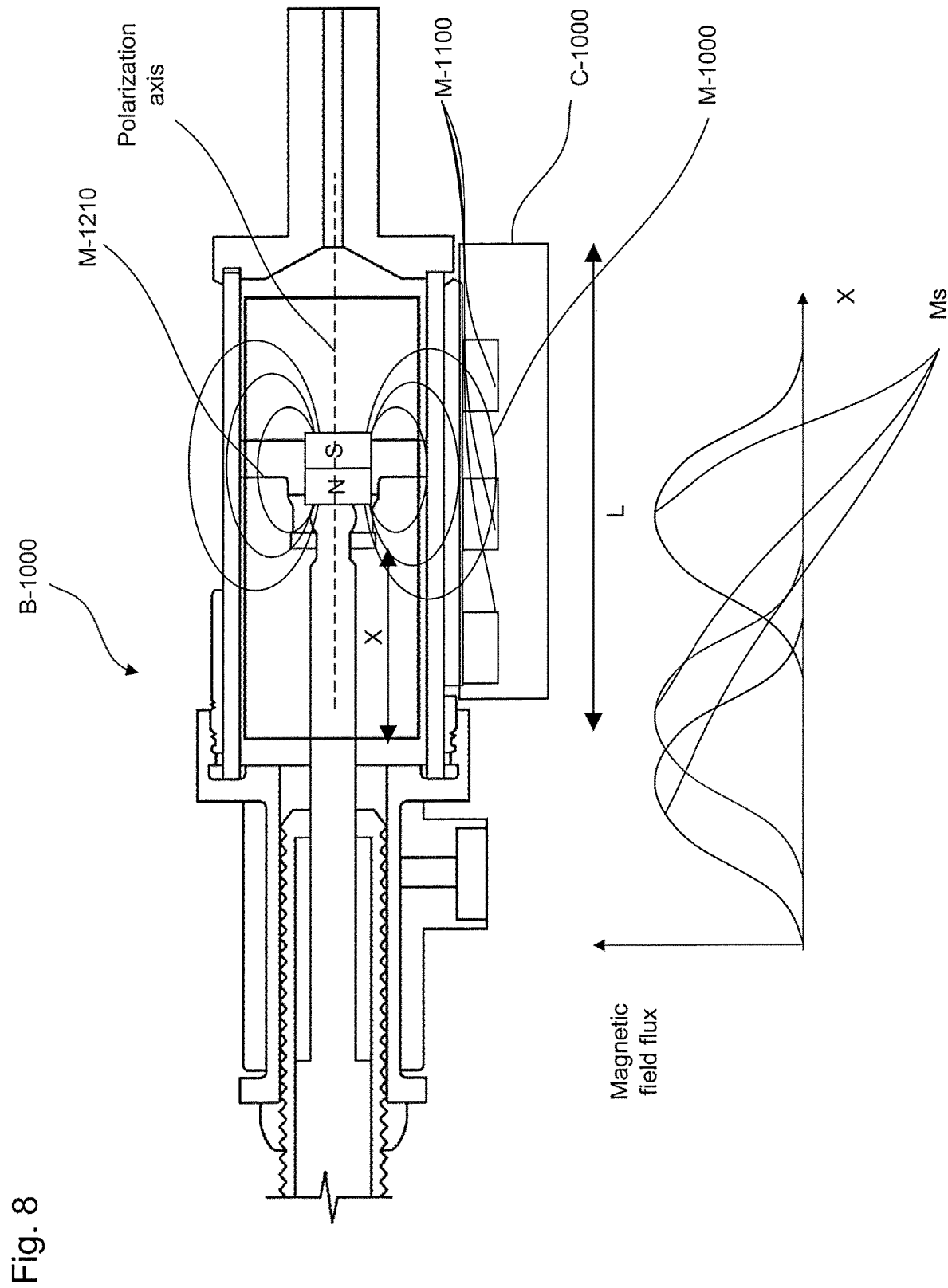
FIG. 8 is a cross sectional view of the drug delivery apparatus with the measuring system relying on magnetic field variations, according to certain aspects of the disclosure.

Alternatively, the contactless interactions can correspond to magnetic field variations and the quantifications of the substance 10 can be performed through measurements of the magnetic variations, as illustrated in FIG. 8.

For example, the dispensing mechanism B-1000 can include a magnetic marker M-1210, e.g. a magnet, affixed on the piston B-1200 and oriented along a polarization axis, e.g. north-south as illustrated in FIG. 8, substantially aligned with the piston course L, and the measuring system C-1000 can include a plurality of magnetic sensors M-1100, e.g. Hall effect sensors, magneto-inductive sensors from Micro-Epsilon, positioned along piston course L and/or on an axis substantially perpendicular to the polarization axis of the magnetic marker M-1210.

The magnetic marker M-1210 can generate magnetic field lines M-1000 that are displaced as the magnetic marker M-1210 is displaced along the piston course L while the plurality of magnetic sensors M-1100 can receive the magnetic field lines M-1000 and provide a plurality of magnetic field signals Ms commensurate with magnetic field intensities. The plurality of magnetic field signals Ms can be received by the data acquisition circuitry C-1400 and the position X of the piston B-1200 can be determined through software instructions executed by the electrical control unit C-1200, as illustrated in FIG. 2.

For example, the software instructions executed by the electrical control unit C-1200 can be written to determine the position X of the piston B-1200 based on the plurality of magnetic field signals Ms via differential measurement methods that focus on a linear response part of each magnetic field signal of the plurality of magnetic field signals Ms. These differential measurement methods can reduce inaccuracy measurements due to temperature and/or humidity variations.

Figure 9:
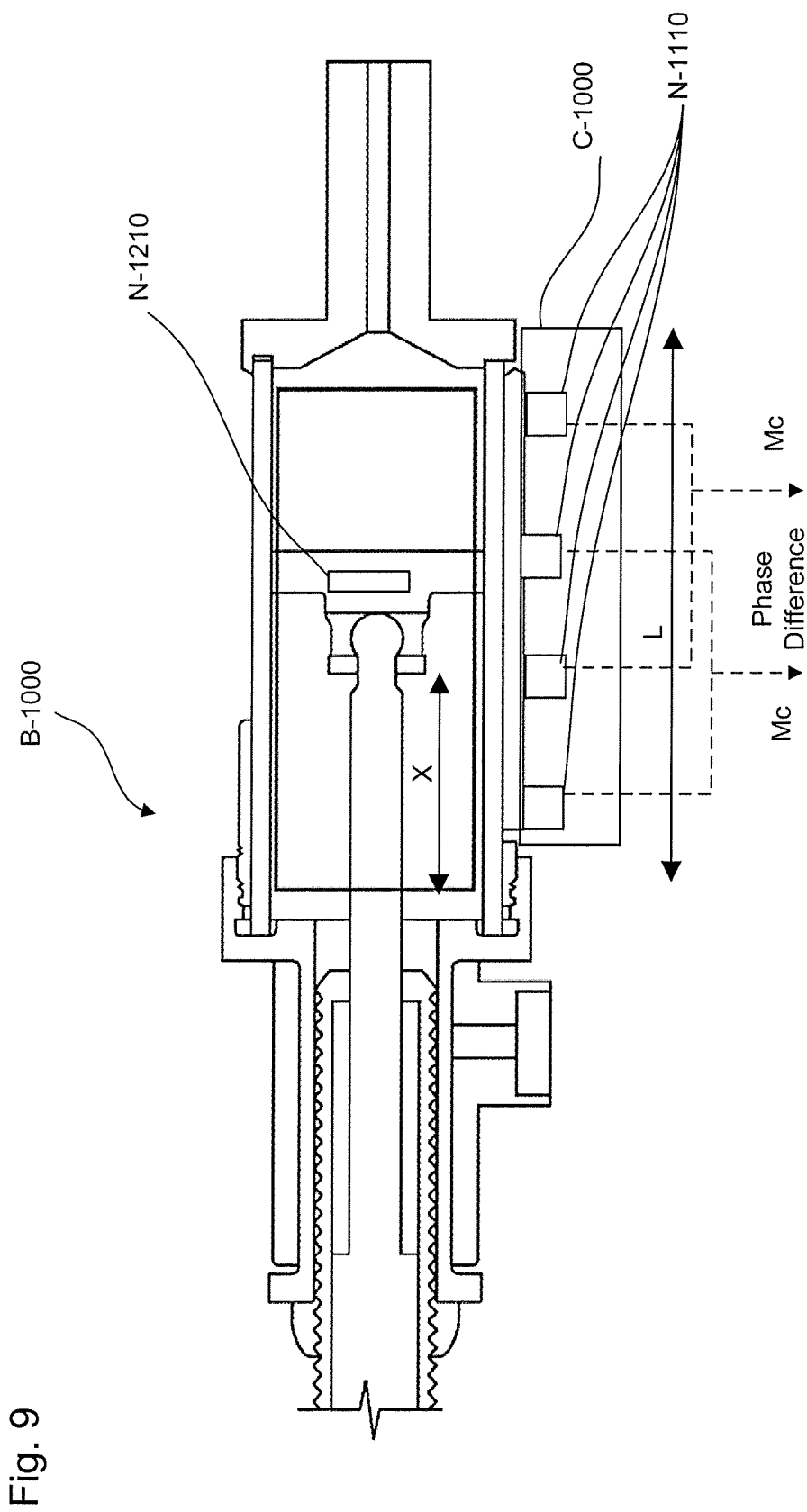
FIG. 9 is a cross sectional view of the drug delivery apparatus with the measuring system relying on capacitance variations, according to certain aspects of the disclosure.

Alternatively, the contactless interactions can correspond to capacitance variations and the quantifications of the substance 10 can be performed through measurements of the capacitance variations, as illustrated in FIG. 9.

For example, the dispensing mechanism B-1000 can include a moving electrode N-1210 affixed on the piston B-1200 and a plurality of fixed electrodes N-1110 positioned along piston course L.

The plurality of fixed electrodes N-1110 can provide a plurality of capacitance signals Mc commensurate with capacitance values between the moving electrode N-1210 and the plurality of fixed electrodes N-1110.

The plurality of fixed electrodes N-1110 can be electrically connected between each other such that the plurality of fixed electrodes N-1110 provides each capacitance signal of the plurality of capacitance signals Mc with a sinusoidal shape and where a predetermined phase difference of $\phi$ between each other, as illustrated in FIG. 9. For example, the plurality of fixed electrodes N-1110 can be electrically connected in two sets of electrodes and have a predetermined phase difference $\phi$ substantially equal to 180° to further enhance precision of the measurement of the position X of the piston B-1200, as illustrated in FIG. 9.

The capacitance signals Mc can be received by the data acquisition circuitry C-1400 and the position X of the piston B-1200 can be determined through software instructions executed by the electrical control unit C-1200.

Figure 10:
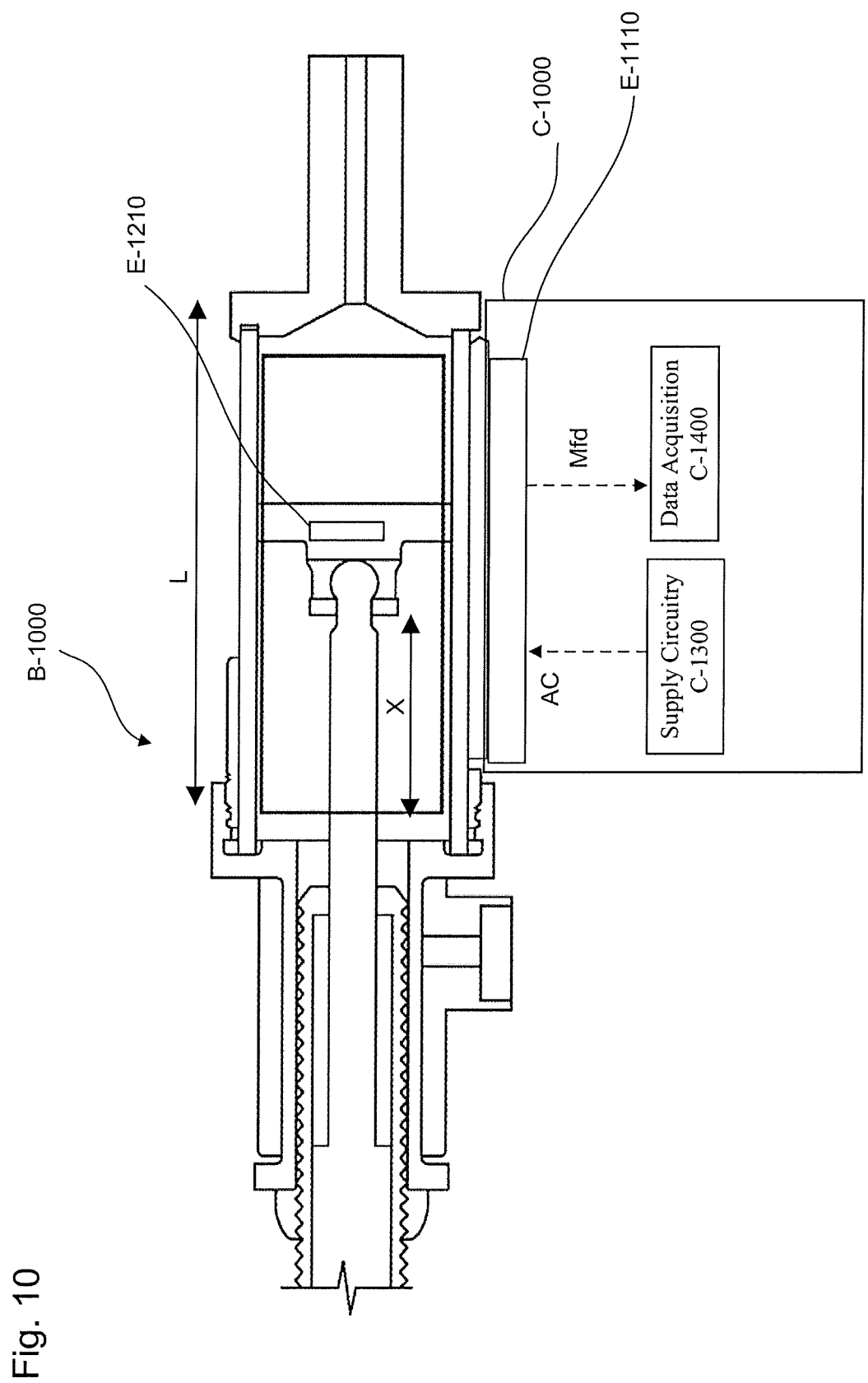
FIG. 10 is a cross sectional view of the drug delivery apparatus with the measuring system relying on eddy-current variations, according to certain aspects of the disclosure.

Alternatively, the contactless interactions can correspond to eddy-current variations and the quantifications of the substance 10 can be performed through measurements of the eddy-current variations, as illustrated in FIG. 10.

For example, the dispensing mechanism B-1000 can include a conductive target E-1210, a metallic part, affixed on the piston B-1200 and a plurality of sensing coils E-1110 positioned along the piston course L. The plurality of sensing coils E-1110 can receive an alternating current AC from the supply circuit C-1300 and the plurality of sensing coils E-1110 can generate an alternating magnetic field that generates in the conductive target E-1210 eddy-currents that produce an opposing magnetic field. The plurality of sensing coils E-1110 can provide feedback signals Mfd commensurate with interactions between the magnetic field generated by the plurality of sensing coils E-1110 and the opposing magnetic field.

The feedback signals can be received by the data acquisition circuitry C-1400 and the position X of the piston B-1200 can be determined through software instructions executed by the electrical control unit C-1200.

Figure 11:
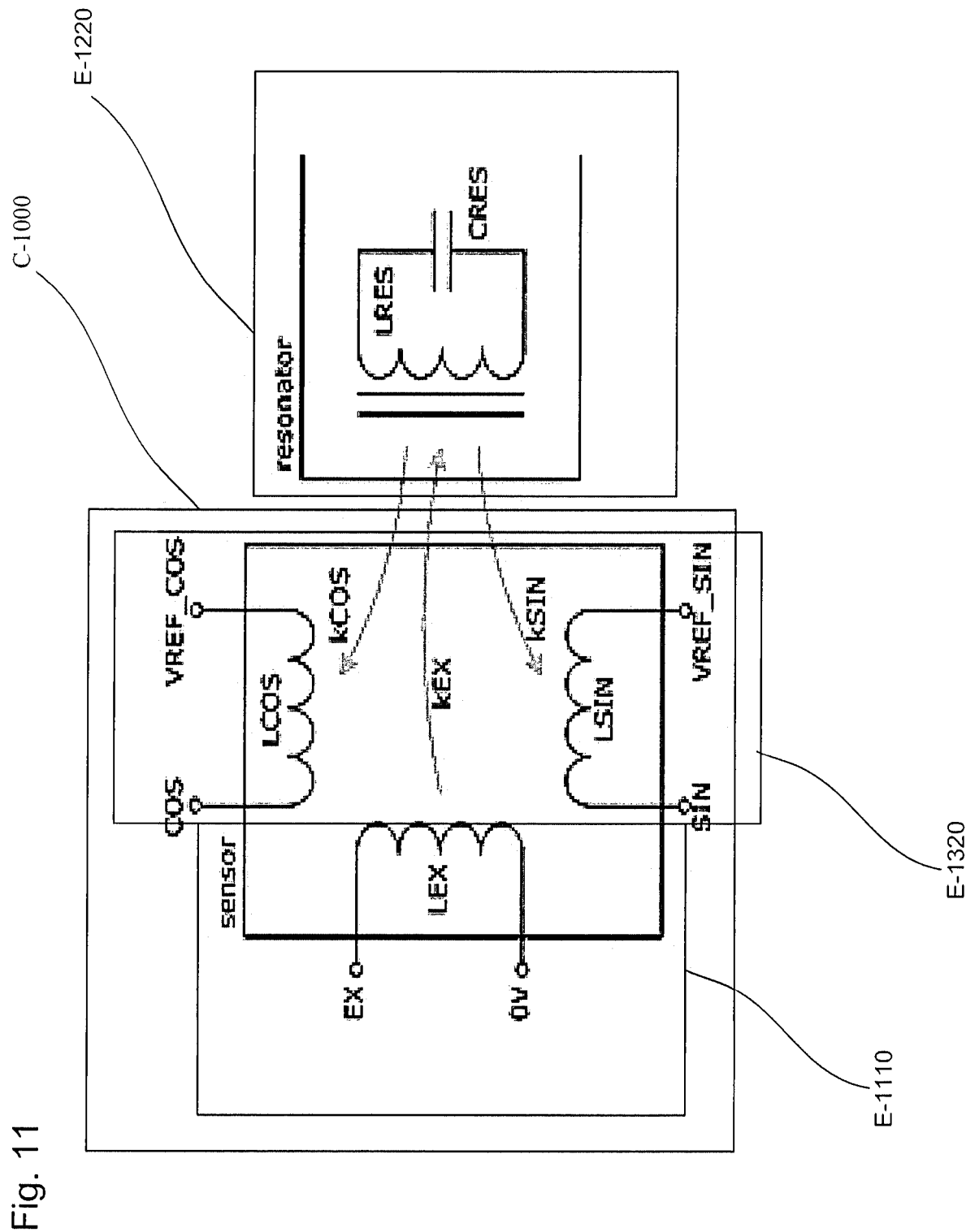
FIG. 11 is a schematic view of the measuring system with a resonator, according to certain aspects of the disclosure.

Alternatively, the conductive target E-1210 can be replaced by a resonator E-1220 that becomes energized by the magnetic field generated by the plurality of sensing coils E-1110 and in return resonates back to the plurality of coils E-1110 to generate coupling factors between the resonator E-1220 and the plurality of sensing coils E-1110, as illustrated in FIG. 11.

In addition, the measuring system C-1000 can include a sensing circuitry E-1320, e.g. COS sensing coil (KCOS) and/or SIN sensing coil (KSIN) as illustrated in FIG. 11, that senses coupling factors between the resonator E-1220 and the plurality of sensing coils E-1110.

The different elements of the electrical control unit C-1200 as well as their interactions and functionality will be described in further detailed in the following paragraphs.

Figure 3:
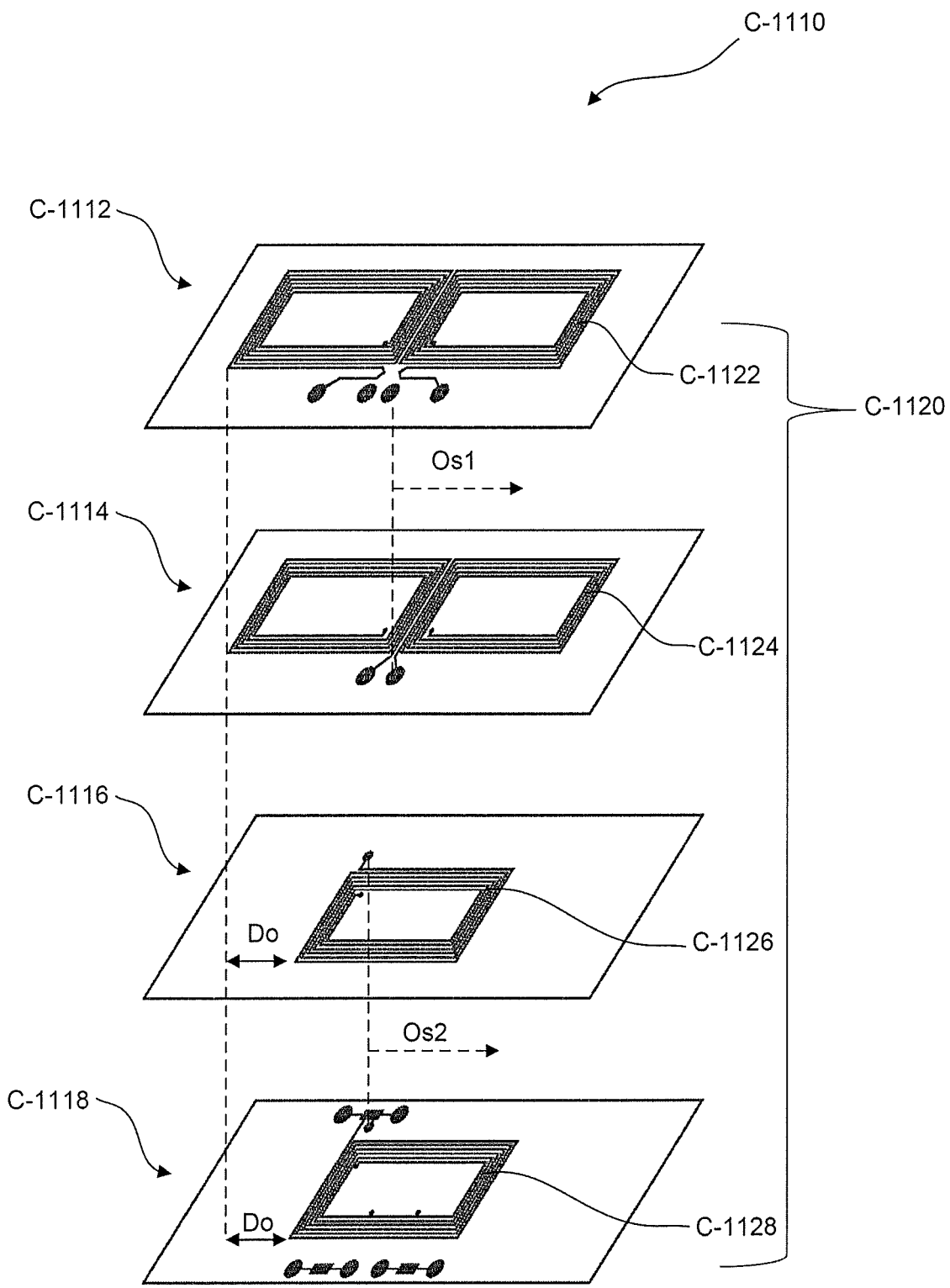
FIG. 3 is an exploded view of an antenna of the measuring system, according to certain aspects of the disclosure.

FIG. 3 is an exploded view of the antenna C-1100 of the drug delivery apparatus 1000, according to certain aspects of the disclosure.

The antenna C-1100 can be a printed circuit board with a multi-layer structure that includes a plurality of layers C-1110 stacked on top of each other and that supports a plurality of sets of coils C-1120.

For example, the antenna C-1100 can include a first layer C-1112 with a first set of coils C-1122, a second layer C-1114 with a second set of coils C-1124, a third layer C-1116 with a third set of coils C-1126, and a fourth layer C-1118 with a fourth set of coils C-1128.

The first, second, third, and fourth sets of coils C-1122, C-1124, C-1126, C-1128 can extend along the piston course L, be electrically connected between each other, and be offset from each other by a predetermined offset distance Do to have each feedback signal of the one or more feedback signals Os commensurate with the position X of the piston B-1200 within a respective part of the piston course L.

For example, the first, second, third, and fourth sets of coils C-1122, C-1124, C-1126, C-1128 can be electrically connected two by two through the supply circuitry C-1300 and be offset by half-lengths to provide a first feedback signal Os1 and a second feedback signal Os2, wherein the first feedback signal Os1 is commensurate with the piston position X within a first half of the piston course L while the second feedback signal Os2 is commensurate with the piston position X within a second half of the piston course L.

The antenna C-1100 can have geometrical configurations, e.g. shape, and/or positioning, to increase measurement precision of the substance quantity Qs being extracted and/or discharged by the drug delivery apparatus 1000.

Figure 12A:
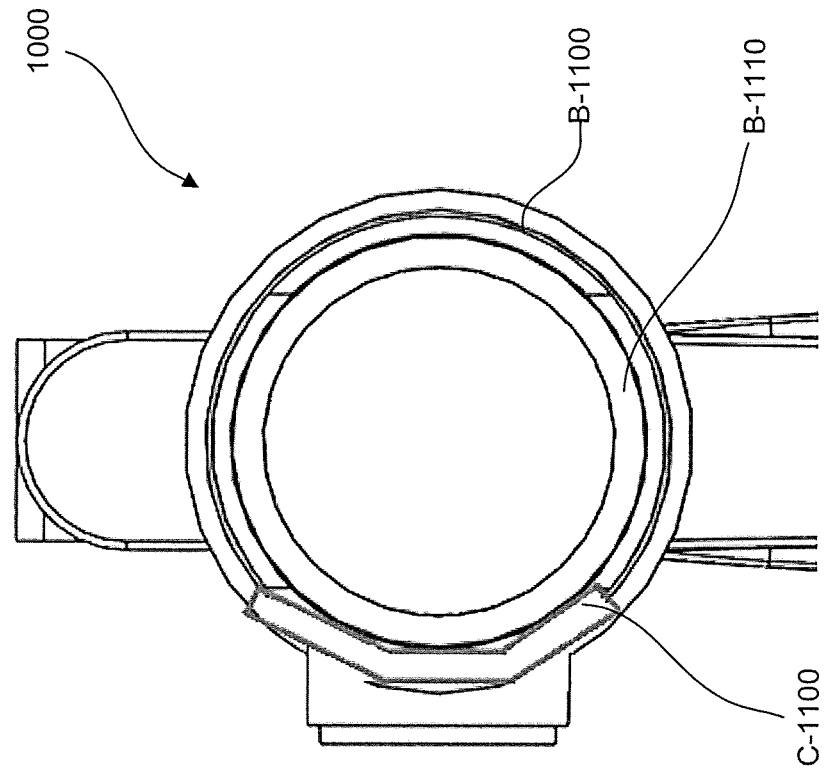
FIG. 12A is a sectional view of the drug delivery apparatus with the measuring system in a first geometrical configuration, according to certain aspects of the disclosure.

In a first geometrical configuration, as illustrated in FIG. 12A, the antenna C-1100 can have a rectangular shape with a substantially rigid structure and be positioned tangentially to an external barrel surface B-1110 of the barrel B-1100 to minimize a distance between the antenna C-1100 and the piston B-1200, for example.

Figure 12B:
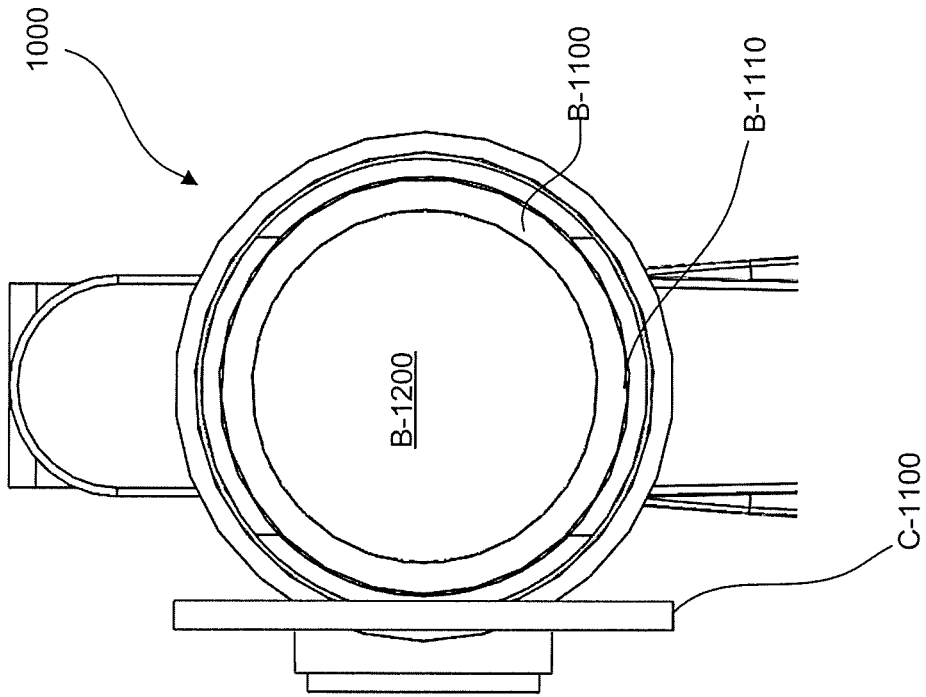
FIG. 12B is a sectional view of the drug delivery apparatus with the measuring system in a second geometrical configuration, according to certain aspects of the disclosure.

In a second geometrical configuration, as illustrated in FIG. 12B, the antenna C-1100 can have a rectangular shape with a flexible and/or semi-flexible structure that follows a curve of the external barrel surface B-1110 to minimize the distance between the antenna C-1100 and the piston B-1200 and maximize the amplitude of the feedback signals Os, for example.

Numerous modifications and variations on the above presented geometrical configurations of the antenna C-1100 are possible in light of the above teachings. It is therefore to be understood that the antenna C-1100 may have different configurations otherwise than as specifically described herein.

In addition, the antenna C-1100 can be placed from the barrel B-1100 at a predetermined distance db, as illustrated in FIG. 1A, sufficiently short to maximize amplitudes of the feedback signals Os but sufficiently large to allow sufficient wall thickness for barrel B-1100 and/or the measuring system C-1000 to be placed inside a housing. For example, the predetermined distance can be between 1 mm and 10 mm, and preferably between 2 mm and 5 mm.

FIGS. 4A-4G are schematic views of a first, a second, a third, a fourth, a fifth, a sixth, and a seventh exemplary coil configuration of the antenna C-1100, according to certain aspects of the disclosure.

The plurality of sets of coils C-1120 can have coil configurations to provide the one or more feedback signals Os with predetermined signal analysis characteristics that increase the accuracy of the values of the piston position X extracted by the electrical control unit C-1200 from the one or more feedback signals Os via software instructions.

The coil configurations can include a coil shape, a longitudinal coil arrangement, a transversal coil arrangement, and/or a winding direction while the predetermined signal analysis characteristics can include a number of signals, bijective conditions, and/or signal amplitude variation as a function of the piston position X.

Figure 4C:
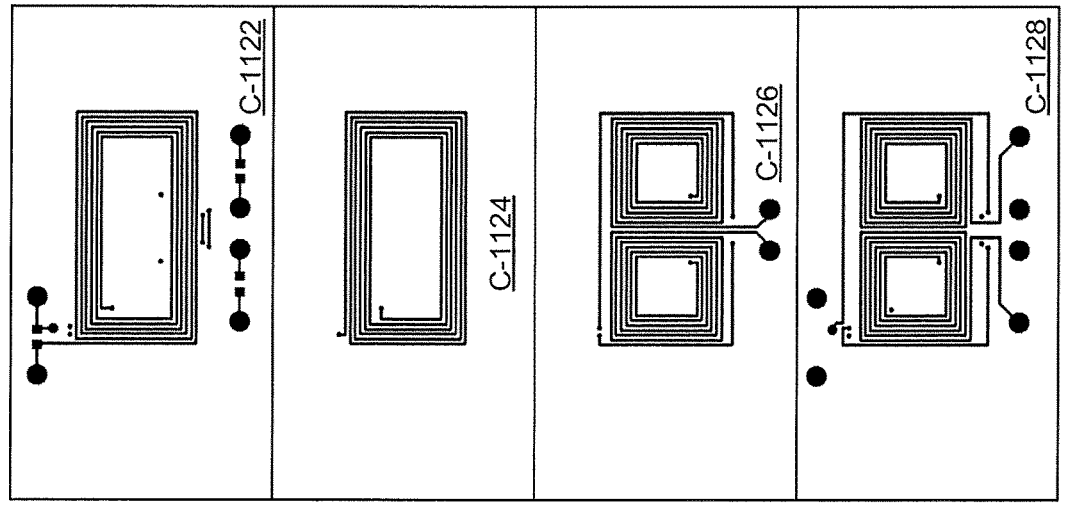
FIG. 4C is a schematic view of a third exemplary coil configuration of the antenna, according to certain aspects of the disclosure.
Figure 4B:
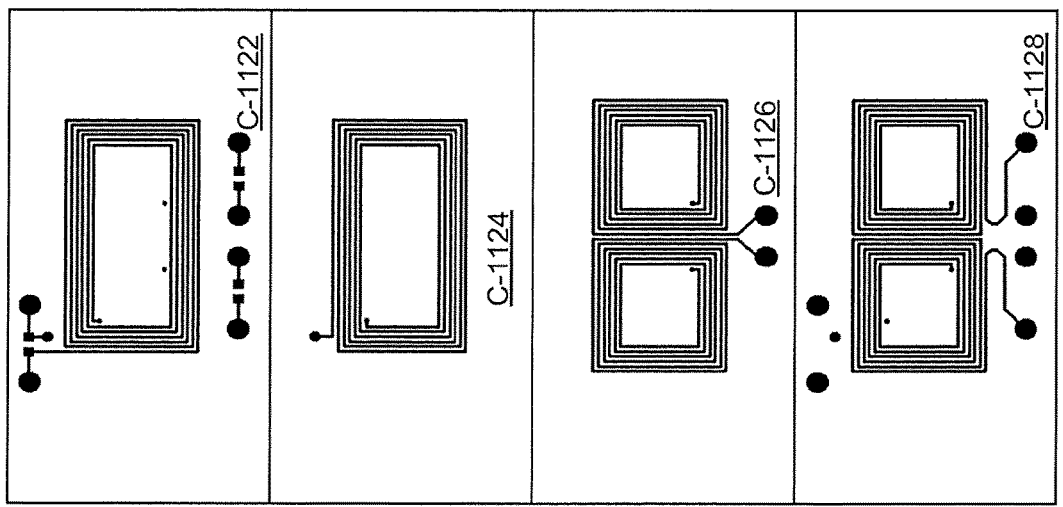
FIG. 4B is a schematic view of a second exemplary coil configuration of the antenna, according to certain aspects of the disclosure.
Figure 4A:
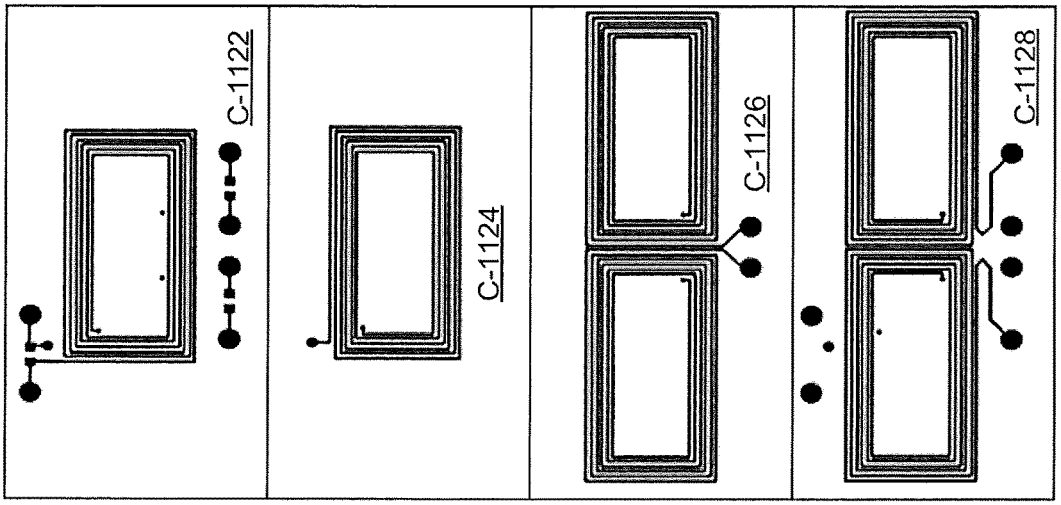
FIG. 4A is a schematic view of a first exemplary coil configuration of the antenna, according to certain aspects of the disclosure.
Figure 4G:
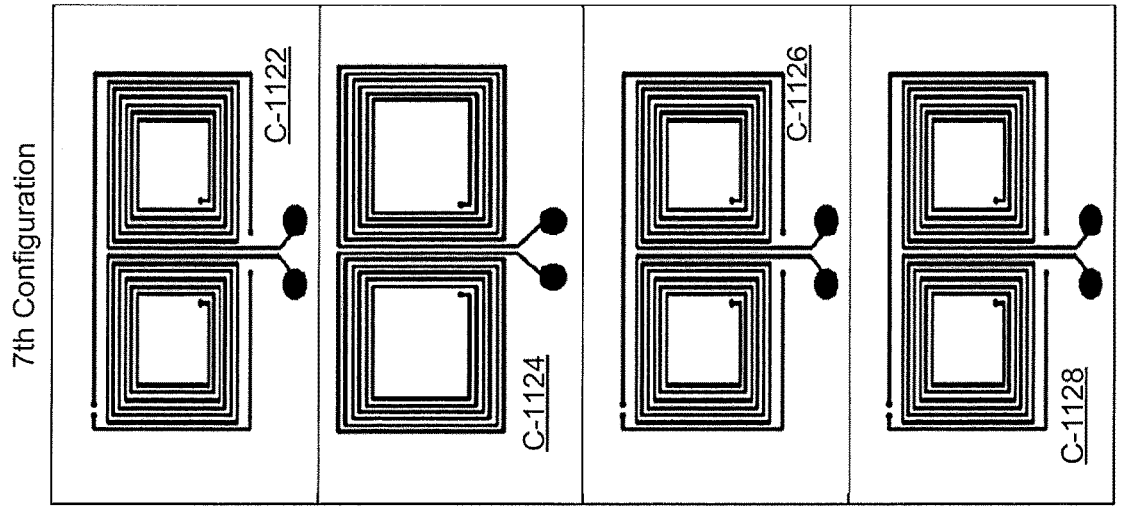
FIG. 4G is a schematic view of a seventh exemplary coil configuration of the antenna, according to certain aspects of the disclosure.

The coil shape can be square, as illustrated in FIGS. 4B-4C for the for the third and fourth sets of coils C-1126 and C-1128, rectangular, as illustrated in FIGS. 4A-4C for the first and second sets of coils C-1122 and C-1124, spherical, as illustrated in FIGS. 4E-4F for first, second, third and fourth sets of coils C-1122, C-1124, C-1126, and C-1128, and/or oval, as illustrated in FIG. 4D for first, second, third, and fourth sets of coils C-1122, C-1124, C-1126, and C-1128.

The longitudinal coil arrangement can be one by one, as illustrated in FIGS. 4A-4E for the first and second sets of coils C-1122 and C-1124, or two by two and side by side, as illustrated in FIGS. 4A-4C for the third and fourth sets of coils C-1126 and C-1128.

The transversal coil arrangement can be aligned wherein two consecutively stacked coils are substantially aligned on top of each other, as illustrated in FIGS. 4A-4C for the first and second sets of coils C-1122 and C-1124, or staggered wherein two consecutively stacked coils are offset from each other, e.g. by a half-length, as illustrated FIGS. 4D-4E for the first and second sets of coils C-1122 and C-1124.

The winding direction can be clock-wise, as illustrated in FIGS. 4A-4F for the first set of coils C-1122, or counter clock-wise, as illustrated in FIGS. 4A-4F for the second set of coils C-1124, for coils arranged one-by-one, co-rotating, as illustrated in FIG. 4F for the first and third sets of coils C-1122 and C-1126, counter-rotating, as illustrated in FIGS. 4A-4C for the third and fourth sets of coils C-1126 and C-1128, for coils arranged two-by-two.

In a $7^{th}$ configuration for the plurality of set of coils C-1120 the first, second, third, and fourth sets of coils C-1122, C-1124, C-1126, and C-1128 can be contra rotating and positioned side by side and placed on top of each other to limit interferences between the plurality of sets of coils C-1120.

Numerous modifications and variations on the above presented coil configurations of the antenna C-1100 are possible in light of the above teachings. It is therefore to be understood that the coils of the antenna C-1100 may have different configurations otherwise than as specifically described herein.

FIG. 5 is a schematic view of a tracking system D-1000 of the drug delivery apparatus 1000, according to certain aspects of the disclosure.

The drug delivery apparatus 1000 can include a tracking system D-1000 to extract, store, and communicate key information K related to the usage of the drug delivery apparatus 1000.

The tracking system D-1000 can include a target identifier D-1100, a substance identifier D-1200, a network controller D-1300, and a supplemental electrical control unit D-2000, which is communicatively-coupled (wire or wireless communication) with each of the target identifier D-1100, the substance identifier D-1200, the network controller D-1300, and the data acquisition circuitry C-1400 of the measuring system C-1000.

The target identifier D-1100 can be any device configured to detect a target marker D-1110 and provide to the supplemental electrical control unit D-2000 target identification signals TIs commensurate with target identification data of the target 20. For example, the target marker D-1110 can be a Radio Frequency Identification (RFID) chip relying on Near-Field Communication (NFC) and/or Ultra High Frequency (UHF) systems and the target identifier D-1100 can be a RFID reader.

The target marker D-1110 can be placed on an ear tag, a collar tag, an ankle tag, and/or a rumen bolus affixed to the target 20.

The target identification data can include any data pertinent to the identification and tracking of the target 20. For example when the target 20 is an animal, the target identification data can include an Animal Identification Number (AIN), an animal code, a herd code, a flock code, a Property Identification Code (PIC), or the like.

According to an embodiment, the above-described target identification data, stored locally to an animal via RFID chip, for example, can be received as target identification signal TIs and processed by the supplemental electrical control unit D-2000 (or similar processing circuitry) to determine if, for instance, the acquired target identification data matches an anticipated identification data. Based upon this matching, or lack thereof, the supplemental electrical control unit D-2000 (or similar) can generate an alert to a farmer, accordingly. Alternatively, the processing circuitry can provide a control signal to the dispensing mechanism B-1000 to deactivate the electrical actuator. The anticipated identification data of an animal can include, among others, an AIN. In an example, a farmer is preparing to inject a substance into a current animal. If the current animal to be administered antibiotic has an AIN of 91, but, according to the farmer's records and as acquired from a server (and database) D-1500 or via a network D-1400, the anticipated AIN of the current animal should be 36, an alert can be provided that a match does not exist between the anticipated identification data and the current target identification data and a control signal can be sent to deactivate the electrical actuator. In another example, the supplemental electrical control unit D-2000 or similar, in coordination with the server (and database) D-1500 via the network D-1400, records the identification data of recently treated animals such that said entries can be queried at a later time. Accordingly, multiple treatments of one animal can be avoided by cross-referencing the recent data entries. For instance, if the supplemental electrical control unit D-2000 determines a match between identification data of an animal to be treated and identification data of a recent entry within data storage, an alert can be generated, and the electrical actuator deactivated, so that the animal is not twice treated.

The substance identifier D-1200 can be any device configured to detect a substance marker D-1210 and provide to the supplemental electrical control unit D-2000 substance identification signals Sis commensurate with a substance identity. For example, the substance marker D-1210 can be a Radio Frequency Identification (RFID) chip relying on Near-Field Communication (NFC) and/or Ultra High Frequency (UHF) systems and the substance identifier D-1200 can be a RFID reader.

In another example, the substance marker D-1210 can be a bar code and the substance identifier D-1200 can be a bar code scanner, as illustrated in FIG. 5. The substance marker D-1210 can be placed on a recipient, e.g. a bottle or a pocket, containing the substance 10.

The substance identification data can include any data pertinent to the identification and tracking of the substance 10. For example when the target 20 is a drug, the substance identification data can include a Drug Identification Number (DIN), a manufacture batch code, or the like.

According to an embodiment, the substance identification data, including, among others, the manufacture batch code, can be processed by the supplemental electrical control unit D-2000 to determine a date the substance 10, or, for instance, antibiotic, was manufactured and what date the substance 10 expires on. For example, if it is determined that the current date of attempted treatment is beyond or near the date of expiration of the antibiotic, as determined from the manufacture batch code, an alert can be generated that the activity and, therefore, utility of the substance 10 may be degraded and the antibiotic should not be used. Concurrently, the processing circuitry can transmit a control signal to deactivate the electrical actuator of the dispensing mechanism B-1000.

In contrast to the above-described local focus of the substance identification information, according to another embodiment, the substance identification data, including, among others, the manufacture batch code, can be considered in context of global data collected at the server (and database) D-1500 via the network D-1400. This global data can include, for instance, information from other farms pointing to the efficacy or not of a substance 10, or related animal-issues therein. In an example, wherein the substance 10 is an antibiotic, it can be imagined that time may elapse between acquiring an antibiotic and administration of the antibiotic by a local farmer to their animals, during which time a bacterium may evolve and become resistant to the antibiotic. Resistance can be determined by evaluating data collected at the server (and database) D-1500 from other farmers indicating animals at said farms have succumbed to illness. Accordingly, as the local farmer prepares to administer the antibiotic to his/her animals, an alert can be generated informing the local farmer that the antibiotic is no longer effective against a specific disease. Moreover, the processing circuitry can transmit a control signal deactivating the electrical actuator of the dispensing mechanism B-1000. For instance, the substance identification data, including the DIN and the manufacture batch code, can be processed by the supplemental electrical control unit D-2000, or similar, and compared to the data collected at the server (and database) D-1500. If the antibiotic has been flagged for within a specific geographic region or for a certain breed of animal, an alert can be generated informing the local farmer that effective protection by the antibiotic of his/her animals will require a new antibiotic. Similar to the above, the electrical actuator of the dispensing mechanism B-1000 can be concurrently deactivated.

According to an embodiment, the target identification data and substance identification data can be evaluated in tandem. For instance, when different antibiotics are appropriate for different animals, data specific to each animal can be stored on an RFID chip, or similar, such that, when beginning a treatment process, the required antibiotic for a specific animal, as determined from the target identification data, can be compared with the substance identification data to ensure a correct antibiotic is being supplied to the animal.

The network controller D-1300 can be any circuitry configured to exchange the key information K, e.g. the target identification data, the substance identification data, and/or the substance quantity Qs administered to the target 20, between the tracking system D-1000, server (and database) D-1500, and an electronic device D-1600 via a network D-1400.

For example, the network controller D-1300 can be as an Intel Ethernet PRO network interface card from Intel Corporation of America, for interfacing with the network D-1400. As can be appreciated, the network D-1400 can be a public network, such as the Internet, or a private network such as an LAN or WAN network, or any combination thereof and can also include PSTN or ISDN sub-networks. The network D-1400 can also be wired, such as an Ethernet network, or can be wireless such as a cellular network including EDGE, 3G and 4G wireless cellular systems. The wireless network can also be WiFi, Bluetooth, or any other wireless form of communication that is known.

Figure 6:
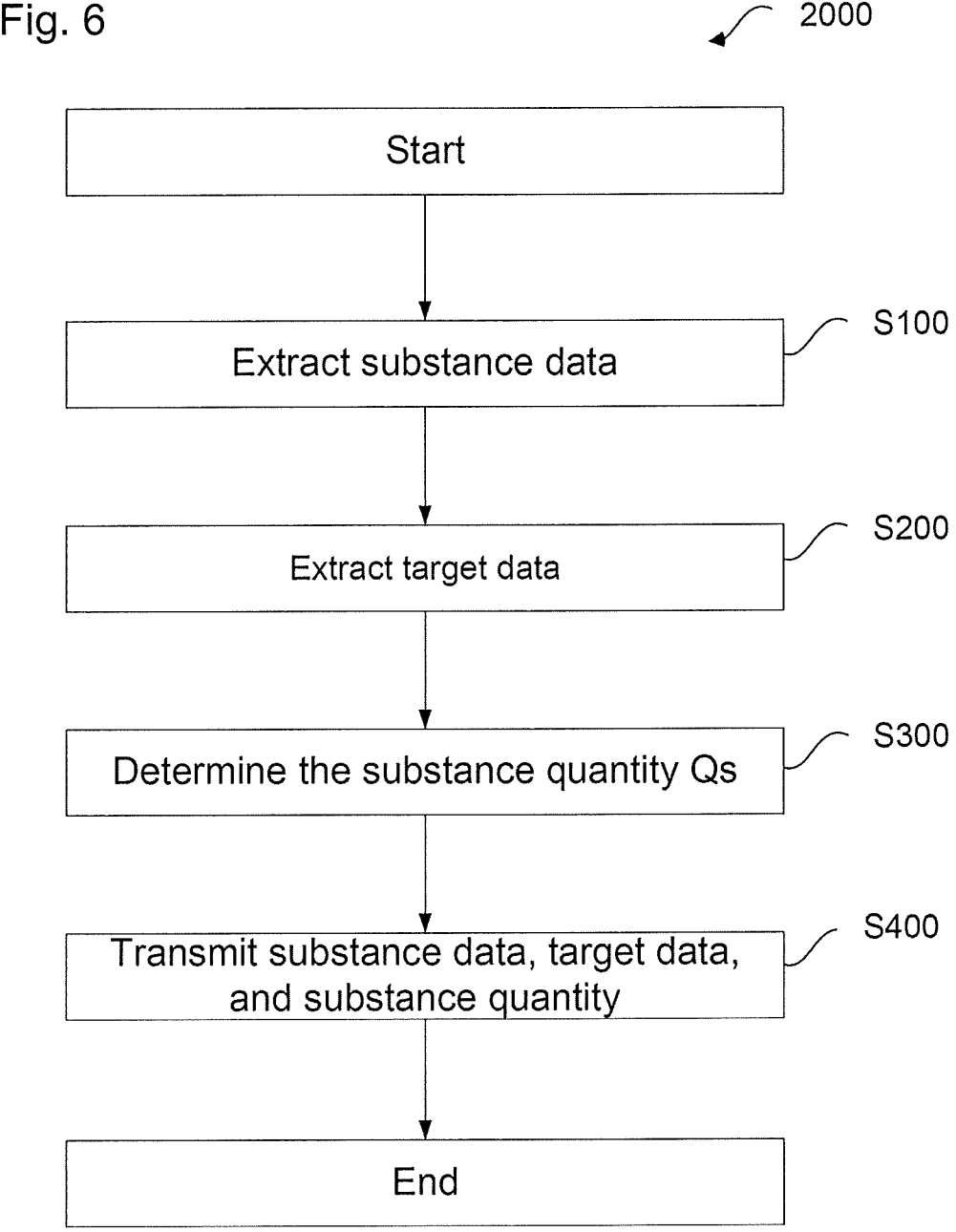
FIG. 6 is a flow chart of a method for operating the drug delivery apparatus, according to certain aspects of the disclosure.

Alternatively, the network controller D-1300 can be integrated onto the supplemental electrical control unit D-2000, as illustrated in FIG. 6.

The server (and database) D-1500 can be configured to store and/or provide access to the key information K about the usage of the drug delivery apparatus 1000, such as an electronic data base, a computer and/or computerized server, data base server or any network host configured to store data.

The electronic device D-1600 can be a computer, a laptop, a smartphone, a tablet, or the like that can store and display the key information K. Similarly, the electronic device D-1600 can be configured to, based upon transmitted signals from the server (and database) D-1500 via the network D-1400 or the key information K and processing thereof, generate an alert, the alert being one or more of an audible alert, visual alert, haptic alert, and the like.

According to an embodiment, the above-described alerts can be provided to the farmer, or user, via control of the electronic device D-1600 by the electrical control unit C-1200, by the supplemental electrical control unit D-2000, by the server (and database) D-1500, and the like.

According to an embodiment, the above-described control signals (e.g. lockout signals) can be provided to the farmer, or user, via control of the drug delivery apparatus 1000 and/or the electrical device D-1600 by the electrical control unit C-1200, by the supplemental electrical control unit D-2000, by the server (and database) D-1500, and the like.

The supplemental electrical control unit D-2000 can have similar functionalities as well as elements as the electrical control unit C-1200 or be replaced by the electrical control unit C-1200 and can, therefore, be used interchangeably to accomplish the tasks described above. Both the electrical control unit C-1200 and the supplemental control unit D-2000 are further detailed in the following paragraphs.

According to another embodiment, information acquired by the drug delivery apparatus 1000 during administration of a substance can be stored and/or processed locally (at drug delivery apparatus 1000) or remotely (at the server (and database) D-1500) or at the tracking system D-1000 for longitudinal evaluation of the wellness of the animal (i.e. target). For instance, the target identification data acquired from an RFID chip local to the animal (e.g. AIN), substance identification data acquired from an RFID chip local to the substance storage unit (e.g. DIN), substance quantity Qs administered as measured by the measuring system C-1000 of the drug delivery apparatus 1000, and other information related to the batch of the substance, the date of administration, the angle of administration, and additional environmental factors, can be transmitted and/or stored locally or remotely for retrospective evaluation of animal wellness. For example, in the case of the substance being an antibiotic, wellness of the animal can be tracked, temporally, from the moment of antibiotic administration and in context of environmental factors recorded at the time of administration. This temporal tracking allows for possible correlation of animal welfare with specific metrics of antibiotic administration and may provide for predictions of animal welfare in other instances.

FIG. 6 is a flow chart of a method for operating the drug delivery apparatus 1000, according to certain aspects of the disclosure.

In a step S100, the substance identification data are extracted via the substance identifier D-1200 and through software instructions executed by the electrical control unit C-1200 and/or the supplemental electrical control unit D-2000.

For example, the substance identifier D-1200 can read the substance marker D-1210 and provide substance reading signals commensurate with the substance identification data to the electrical control unit C-1200 and/or the supplemental electrical control unit D-2000.

In addition, the substance identification data can be recorded on a memory C-1204 of the electrical control unit C-1200 and/or the supplemental electrical control unit D-2000.

In a step S200, the target 20 is detected and the target identification data are extracted via the target identifier D-1100 and through software instructions executed by the electrical control unit C-1200 and/or the supplemental electrical control unit D-2000.

For example, the target identifier D-1100 can detect and read the substance marker D-1210 and provide target reading signals commensurate with the target identification data to the electrical control unit C-1200 and/or the supplemental electrical control unit D-2000.

In addition, the target identification data can be recorded on the memory C-1204 of the electrical control unit C-1200 and/or the supplemental electrical control unit D-2000.

Immediately following step S200, extracted substance data and extracted target data can be evaluated by the electrical control unit C-1200 and/or the supplemental electrical control unit D-2000 to verify correct substance dispensation and, if necessary, intervene by generating an alert and deactivating the electrical actuator of the dispensing mechanism B-1000, as was outlined above with respect to FIG. 5.

In a step S300, the substance quantity Qs is determined via the measuring system C-1000 and through software instructions executed by the electrical control unit C-1200.

For example, the antenna C-1100 can provide the output currents Os based on the electromagnetic interactions between the piston B-1200 and the antenna C-1100. The data acquisition circuitry C-1400 can receive the output currents Os and provide to the electrical control unit C-1200 frequency reading signals commensurate with the resonant frequency Fr of the output currents Os based on the output currents Os. The electrical control unit C-1200 can receive the frequency readings and determine the piston position X based on the frequency readings and consequently the substance quantity Qs delivered by the drug delivery apparatus 1000.

In a step S400, the target identification data, the substance identification data, and the substance quantity Qs are transmitted to the electronic device D-1600 and/or the server (and database) D-1500 via the network controller D-1300 and through software instructions executed by the electrical control unit C-1200.

Alternatively, the target identification data, the substance identification data, and/or the substance quantity Qs can be first recorded on a memory C-1204 of the electrical control unit C-1200 and be later transmitted to the electronic device D-1600 and/or the server (and database) D-1500 via the network controller D-1300 and through software instructions executed by the electrical control unit C-1200.

In addition, due to the practicability of the measuring system C-1000 and/or the tracking system D-1000, e.g. light weight, portability, absence on reliance of mechanical systems, low energy consumption, and/or no need to be connected to a power grid system, the measuring system C-1000 and/or the tracking system D-1000 can be retrofitted to an already manufactured drug delivery apparatus, e.g. already in use and/or in production drug delivery apparatus. For example, the measuring system C-1000 and/or the tracking system D-1000 can be retroactively incorporated to the manufactured drug delivery apparatus by being fastened onto the dispensing mechanism B-1000 and/or the stock A-1000 using fastening devices such as bolts, rivets, adhesives, glues or the combination thereof.

Figure 7:
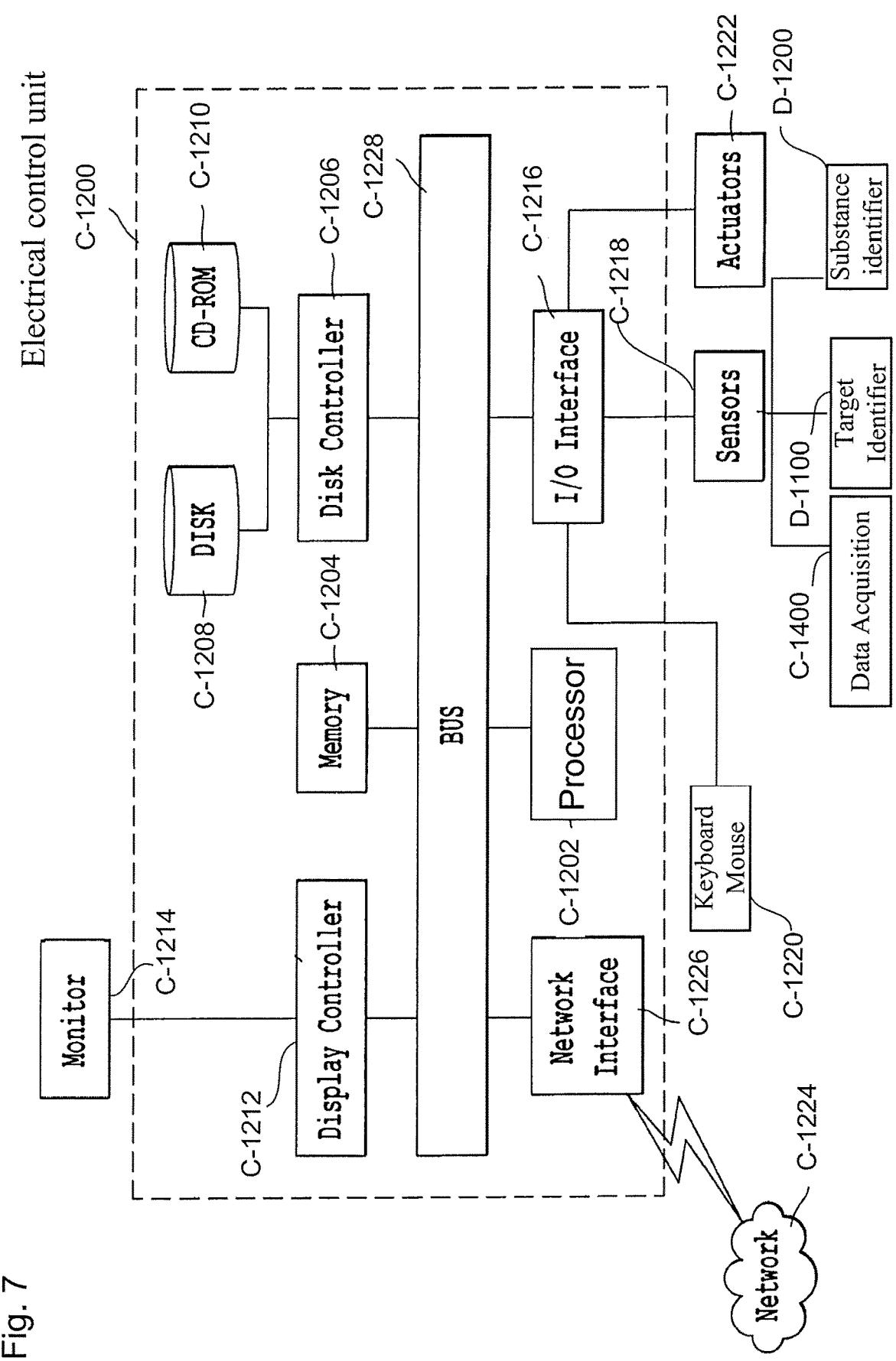
FIG. 7 is a schematic view of a hardware diagram of an electrical control unit of the drug delivery apparatus, according to certain aspects of the disclosure.

FIG. 7 is a schematic view of a hardware diagram of the electrical control unit C-1200 of the drug delivery apparatus 1000. Note that, in one embodiment, FIG. 7 also shows the hardware diagram of the supplemental electrical control unit D-2000. Note that, in one embodiment, FIG. 7 also shows the hardware diagram of the server (and database) D-1500 (and in particular, at least, monitor C-1214, display controller C-1212, disk C-1208, CD-ROM C-1210, disk controller C-1206, memory C-1204, bus C-1228, processor C-1202, network interface C-1226, network C-1224, I/O interface C-1216, and keyboard/mouse C-1220).

As shown in FIG. 7, systems, operations, and processes in accordance with this disclosure may be implemented using processing circuitry such as a processor C-1202 or at least one application specific processor (ASP). The processor C-1202 may utilize a computer readable storage medium, such as a memory C-1204 (e.g., ROM, EPROM, EEPROM, flash memory, static memory, DRAM, SDRAM, and their equivalents), configured to control the processor C-1202 to perform and/or control the systems, operations, and processes of this disclosure. Other storage mediums may be controlled via a disk controller C-1206, which may control a hard disk drive C-1208 or optical disk drive C-1210.

The processor C-1202 or aspects thereof, in an alternate embodiment, can include or exclusively include a logic device for augmenting or fully implementing this disclosure. Such a logic device includes, but is not limited to, an application-specific integrated circuit (ASIC), a field programmable gate array (FPGA), a generic-array of logic (GAL), and their equivalents. The processor C-1202 may be a separate device or a single processing mechanism. Further, this disclosure may benefit form parallel processing capabilities of a multi-cored processor.

In another aspect, results of processing in accordance with this disclosure may be displayed via a display controller C-1212 to a monitor C-1214 that may be peripheral to or part of the electrical control unit C-1200. Moreover, the monitor C-1214 may be provided with a touch-sensitive interface to a command/instruction interface. The display controller C-1212 may also include at least one graphic processing unit for improved computational efficiency. Additionally, the electrical control unit C-1200 may include an I/O (input/output) interface C-1216, provided for inputting sensor data from sensors C-1218 and for outputting orders to actuators C-1222. The sensors C-1218 and actuators C-1222 are illustrative of any of the sensors and actuators described in this disclosure. For example, the sensors can be the data acquisition circuitry C-1400 for the electrical control unit C-1200 and the supplemental electrical control unit D-2000, as well as the target identifier D-1100 and the substance identifier D-1200 for the supplemental electrical control unit D-2000.

Further, other input devices may be connected to an I/O interface C-1216 as peripherals or as part of the electrical control unit C-1200. For example, a keyboard or a pointing device such as a mouse C-1220 may control parameters of the various processes and algorithms of this disclosure, and may be connected to the I/O interface C-1216 to provide additional functionality and configuration options, or to control display characteristics. Actuators C-1222 which may be embodied in any of the elements of the apparatuses described in this disclosure may also be connected to the I/O interface C-1216.

The above-noted hardware components may be coupled to the network C-1224, such as the Internet or a local intranet, via a network interface C-1226 for the transmission or reception of data, including controllable parameters to a mobile device. A central BUS C-1228 may be provided to connect the above-noted hardware components together, and to provide at least one path for digital communication there between.

Embodiments of the present disclosure may also be as set forth in the following parentheticals.

(1) A drug delivery apparatus, comprising a barrel to contain a substance, a piston slidable in the barrel along a piston course, a supply circuit to provide input currents, an antenna affixed along the barrel including a circuit board with a plurality of layers stacked on top of each other and connected to the supply circuit, and a plurality of coils on the plurality of layers to receive the input currents, generate an inductance with the piston, and provide output currents commensurate with the inductance, a target identifier to detect a target marker and provide target reading signals commensurate with target information, a substance identifier to read a substance marker and provide substance reading signals commensurate with substance information, and processing circuitry configured to receive the output currents, the target reading signals, and the substance reading signals, determine a quantity of the substance inside the barrel based on the output currents, extract the target information based on the target reading signals, and extract the substance information based on the substance reading signals.

(2) The drug delivery apparatus of (1), wherein the plurality of coils extends along the piston course.

(3) The drug delivery apparatus of either (1) or (2), wherein at least two coils of the plurality of coils are offset by a predetermined offset distance from each other to provide a first output current commensurate with the piston position within a first part of the piston course and a second output current commensurate with the piston position within a second part of the piston course.

(4) The drug delivery apparatus of any of (1) to (3), wherein the offset distance is substantially equal to half of a width of the at least two coils.

(5) The drug delivery apparatus of any of (1) to (4), wherein the circuit board further includes a first layer with a first single rectangular coil, a second layer with a second single rectangular coil, a third layer with a first pair of rectangular coils electrically connected to the first rectangular coil and offset by the predetermined offset distance to provide the first output current, and a fourth layer with a second pair of rectangular coils electrically connected to the second rectangular coil and offset by the predetermined offset distance to provide the second output current.

(6) The drug delivery apparatus of any of (1) to (5), wherein the target marker is a radio frequency identification chip and the target identifier is configured to read the radio frequency identification chip.

(7) The drug delivery apparatus of any of (1) to (6), wherein the substance marker is a radio frequency identification chip placed on a container containing the substance and the substance identifier is configured to read the radio frequency identification chip.

(8) The drug delivery apparatus of any of (1) to (7), further comprising a network controller configured to send the quantity of substance, the target information, and the substance information to at least one of a data base and an electronic device.

(9) A drug delivery apparatus, comprising a barrel to contain a substance, a piston slidable in the barrel along a piston course, a supply circuit to provide input currents, an antenna affixed along the barrel including a circuit board with a plurality layers stacked on top of each other and connected to the supply circuit, and a plurality of coils on the plurality of layers to receive the input currents, generate an inductance with the piston, and provide output currents commensurate with the inductance, and processing circuitry connected to the plurality of coils and configured to receive the output currents, and determine a quantity of the substance inside the barrel based on the output currents.

(10) The drug delivery apparatus of (9), wherein the plurality of coils extends along the piston course.

(11) The drug delivery apparatus of either (9) or (10), wherein at least two coils of the plurality of coils are offset by a predetermined offset distance from each other to provide a first output current commensurate with the piston position within a first part of the piston course and a second output current commensurate with the piston position within a second part of the piston course.

(12) The drug delivery apparatus of any of (9) to (11), wherein the offset distance is substantially equal to half of a width the at least two coils.

(13) The drug delivery apparatus of any of (9) to (12), wherein the circuit board further includes a first layer with a first single rectangular coil, a second layer with a second single rectangular coil, a third layer with a first pair of rectangular coils electrically connected to the first rectangular coil and offset by the predetermined offset distance to provide the first output current, and a fourth layer with a second pair of rectangular coils electrically connected to the second rectangular coil and offset by the predetermined offset distance to provide the second output current.

(14) A drug delivery apparatus, comprising a barrel to contain a substance, a piston slidable in the barrel along a piston course, a measuring system affixed along the barrel to generate a contactless interaction with the piston, and provide output currents commensurate with a quantification of the contactless interaction, and processing circuitry configured to receive the output currents, and determine a variable dependent on a position of the piston inside the barrel based on the output currents.

(15) The drug delivery apparatus of (14), wherein the contactless interaction is an inductance interaction and the measuring system includes a plurality of coils to generate the inductance interaction.

(16) The drug delivery apparatus of either (14) or (15), wherein the piston includes an inductance marker.

(17) The drug delivery apparatus of any of (14) to (16), wherein the contactless interaction is a magnetic field and the measuring system includes magnetic field sensors to sense the magnetic field.

(18) The drug delivery apparatus of any of (14) to (17), wherein the piston includes a magnetic marker to generate the magnetic field.

(19) The drug delivery apparatus of any of (14) to (18), wherein the contactless interaction is a magneto-inductive interaction and the measuring system includes magneto-inductive sensors, for example, displacement sensors.

(20) The drug delivery apparatus of any of (14) to (19), wherein the contactless interaction is a sonic interaction and the measuring system includes a microwave generator.

(21) The drug delivery apparatus of any of (14) to (20), wherein the contactless interaction is an optical interaction and the measuring system includes an optical sensor.

(22) A method for operating a drug delivery apparatus that delivers a substance onto a target comprising extracting substance identification data through a substance identifier of the drug delivery apparatus and a substance marker of the substance, extracting a target data through a target identifier of the drug delivery apparatus and a target marker of the target, delivering the substance through a dispensing mechanism of the drug delivery apparatus, determining a quantity of substance delivered through a measuring system of the drug delivery apparatus, and recording the substance identification data, the target data, and the quantity of substance delivered through circuitry of the drug delivery apparatus.

(23) The method of (22), further comprising providing input currents through a supply circuit of the measuring system, receiving the input currents through a plurality of coils of the measuring system, generating inductance interactions between the plurality of coils and a piston of the dispensing system, and providing output currents commensurate with the inductance interactions.

(24) The method of either (22) or (23), wherein the drug delivery apparatus comprises a barrel to contain the substance, a piston slidable in the barrel along a piston course, and a measuring system affixed along the barrel.

(25) The method of any of (22) to (24), further comprising generating with the measuring system a contactless interaction with the piston.

(26) The method of any of (22) to (25), further comprising generating with the measuring system output currents commensurate with a quantification of the contactless interaction.

(27) The method of any of (22) to (26), wherein the contactless interaction is an inductance interaction and the measuring system includes a plurality of coils to generate the inductance interaction.

(28) The method of any of (22) to (27), wherein the piston includes an inductance marker.

(29) The method of any of (22) to (28), wherein the contactless interaction is a magnetic field and the measuring system includes magnetic field sensors to sense the magnetic field.

(30) The method of any of (22) to (29), wherein the piston includes a magnetic marker to generate the magnetic field.

(31) The method of any of (22) to (29), wherein the contactless interaction is a magneto-inductive interaction and the measuring system includes magneto-inductive sensors, for example, displacement sensors.

(32) The method of any of (22) to (31), wherein the contactless interaction is a sonic interaction and the measuring system includes a microwave generator.

(33) The method of any of (22) to (32), wherein the contactless interaction is an optical interaction and the measuring system includes an optical sensor.

The foregoing discussion discloses and describes merely exemplary embodiments of an object of the present disclosure. As will be understood by those skilled in the art, an object of the present disclosure may be embodied in other specific forms without departing from the spirit or essential characteristics thereof. Accordingly, the present disclosure is intended to be illustrative, but not limiting of the scope of an object of the present disclosure as well as the claims.

Numerous modifications and variations on the present disclosure are possible in light of the above teachings. It is therefore to be understood that within the scope of the appended claims, the disclosure may be practiced otherwise than as specifically described herein.

What is claimed is:

1. A drug delivery apparatus, comprising:
    a barrel to contain a substance;
    a piston slidable in the barrel along a piston course;
    a supply circuit to provide input currents;
    an antenna affixed along the barrel including:
        a circuit board with a plurality of layers stacked on top of each other and connected to the supply circuit, and
        a plurality of sets of coils on the plurality of layers extending along the piston course to
            receive the input currents,
            generate an inductance with the piston, and
            provide output currents commensurate with the inductance;
    a target identifier to detect a target marker and provide target reading signals commensurate with target information;
    a substance identifier to read a substance marker and provide substance reading signals commensurate with substance information; and
    processing circuitry configured to
        receive the output currents, the target reading signals, and the substance reading signals,
        determine a quantity of the substance inside the barrel based on the output currents,
        extract the target information based on the target reading signals, and
        extract the substance information based on the substance reading signals.

2. The drug delivery apparatus of claim 1, wherein the plurality of sets of coils extends along the piston course so as not to surround the piston.

3. The drug delivery apparatus of claim 1, wherein at least two coils of the plurality of sets of coils are offset by a predetermined offset distance from each other to provide a first output current commensurate with a piston position within a first part of the piston course and a second output current commensurate with the piston position within a second part of the piston course.

4. The drug delivery apparatus of claim 3, wherein the predetermined offset distance is substantially equal to half of a width of the at least two coils.

5. The drug delivery apparatus of claim 1, wherein the circuit board further includes:
    a first layer with a first single rectangular coil;
    a second layer with a second single rectangular coil;
    a third layer with a first pair of rectangular coils electrically connected to the first rectangular coil and offset by a predetermined offset distance to provide a first output current; and a fourth layer with a second pair of rectangular coils electrically connected to the second rectangular coil and offset by the predetermined offset distance to provide a second output current.

6. The drug delivery apparatus of claim 1, wherein the target marker is a radio frequency identification chip and the target identifier is configured to read the radio frequency identification chip.

7. The drug delivery apparatus of claim 1, wherein the substance marker is a radio frequency identification chip placed on the barrel containing the substance and the substance identifier is configured to read the radio frequency identification chip.

8. The drug delivery apparatus of claim 1, further comprising a network controller configured to send the quantity of the substance, the target information, and the substance information to at least one of a data base and an electronic device.

9. A drug delivery apparatus, comprising:
a barrel to contain a substance;
a piston slidable in the barrel along a piston course;
a supply circuit to provide input currents;
an antenna affixed along the barrel including:
 a circuit board with a plurality of layers stacked on top of each other and connected to the supply circuit, and
 a plurality of sets of coils on the plurality of layers extending along the piston course to
  receive the input currents,
  generate an inductance with the piston, and
  provide output currents commensurate with the inductance; and
processing circuitry connected to the plurality of sets of coils and configured to
 receive the output currents, and
 determine a quantity of the substance inside the barrel based on the output currents.

10. The drug delivery apparatus of claim 9, wherein the plurality of sets of coils extends along the piston course so as not to surround the piston.

11. The drug delivery apparatus of claim 10, wherein at least two coils of the plurality of sets of coils are offset by a predetermined offset distance from each other to provide a first output current commensurate with a piston position within a first part of the piston course and a second output current commensurate with the piston position within a second part of the piston course.

12. The drug delivery apparatus of claim 11, wherein the offset distance is substantially equal to half of a width the at least two coils.

13. The drug delivery apparatus of claim 12, wherein the circuit board further includes:
a first layer with a first single rectangular coil;
a second layer with a second single rectangular coil;
a third layer with a first pair of rectangular coils electrically connected to the first rectangular coil and offset by the predetermined offset distance to provide the first output current; and
a fourth layer with a second pair of rectangular coils electrically connected to the second rectangular coil and offset by the predetermined offset distance to provide the second output current.

14. A drug delivery apparatus, comprising:
a barrel to contain a substance;
a piston slidable in the barrel along a piston course;
a measuring system that includes a plurality of sets of coils extending along the piston course, the measuring system being affixed along the barrel to
 generate a contactless interaction with the piston, and
 provide output currents commensurate with a quantification of the contactless interaction; and
processing circuitry configured to
 receive the output currents, and
 determine a variable dependent on a position of the piston inside the barrel based on the output currents.

15. The drug delivery apparatus of claim 14, wherein the contactless interaction is an inductance interaction and the measuring system includes the plurality of sets of coils to generate the inductance interaction.

16. The drug delivery apparatus of claim 15, wherein the piston includes an inductance marker.

17. The drug delivery apparatus of claim 14, wherein the contactless interaction is a magnetic field and the measuring system includes magnetic field sensors to sense the magnetic field.

18. The drug delivery apparatus of claim 17, wherein the piston includes a magnetic marker to generate the magnetic field.

19. The drug delivery apparatus of claim 14, wherein the contactless interaction is a magneto-inductive interaction and the measuring system includes magneto-inductive sensors.

20. The drug delivery apparatus of claim 14, wherein the contactless interaction is a sonic interaction and the measuring system includes a microwave generator.

* * * * *